(12) United States Patent
Isaacson

(10) Patent No.: US 12,340,887 B2
(45) Date of Patent: Jun. 24, 2025

(54) SYSTEM, METHOD, AND PRODUCT FOR IDENTIFYING A LUMEN

(71) Applicant: Becton, Dickinson and Company, Franklin Lakes, NJ (US)

(72) Inventor: Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 945 days.

(21) Appl. No.: 17/421,958

(22) PCT Filed: Feb. 4, 2020

(86) PCT No.: PCT/US2020/016546
§ 371 (c)(1),
(2) Date: Jul. 9, 2021

(87) PCT Pub. No.: WO2020/163304
PCT Pub. Date: Aug. 13, 2020

(65) Prior Publication Data
US 2022/0115106 A1   Apr. 14, 2022

Related U.S. Application Data

(60) Provisional application No. 62/800,609, filed on Feb. 4, 2019.

(51) Int. Cl.
*G16H 20/17* (2018.01)
*A61M 5/14* (2006.01)
(Continued)

(52) U.S. Cl.
CPC .......... *G16H 20/17* (2018.01); *A61M 5/1408* (2013.01); *A61M 5/1409* (2013.01);
(Continued)

(58) Field of Classification Search
CPC ........ G16H 20/17; G16H 40/67; G16H 20/13; G16H 40/63; A61M 5/1408;
(Continued)

(56) References Cited

U.S. PATENT DOCUMENTS

| | | |
|---|---|---|
| 7,990,251 B1 | 8/2011 | Ford, Jr. |
| 10,747,851 B2 | 8/2020 | Nackaerts |

(Continued)

FOREIGN PATENT DOCUMENTS

| | | |
|---|---|---|
| CN | 205549221 U | 9/2016 |
| CN | 108853636 A | 11/2018 |

(Continued)

OTHER PUBLICATIONS

N Porat et al.: "Use of colour-coded tabels for intravenous high-risk medications and lines to improve patient safety"; Quality and Safety in Health Care, vol. 18, No. 6; Dec. 1, 2019; pp. 505-509; ISSN:1475-3898.

*Primary Examiner* — James J Yang
*Assistant Examiner* — Anthony D Afrifa-Kyei
(74) *Attorney, Agent, or Firm* — The Webb Law Firm

(57) ABSTRACT

A visual indicator of a smart device and a visual indicator of a medication source device may be controlled to produce a same type of visual output based on a communication established between the medication source device and the smart device, The medication source device may be connected to a lumen, the smart device may be configured to be connected to the lumen, and the same type of visual output may be associated with the lumen. A compatibility of a first type of medication delivered or scheduled to be delivered via the lumen to a patient and a second type of medication delivered or scheduled to be delivered via the lumen to the patient may be determined to an indication of whether the (Continued)

second type of medication is compatible for delivery via the same lumen associated with the same type of visual output.

26 Claims, 13 Drawing Sheets

(51) Int. Cl.
*A61M 5/168* (2006.01)
*G16H 40/67* (2018.01)

(52) U.S. Cl.
CPC ........ *A61M 5/16831* (2013.01); *G16H 40/67* (2018.01); *A61M 2005/16863* (2013.01); *A61M 2205/3313* (2013.01); *A61M 2205/3569* (2013.01); *A61M 2205/502* (2013.01); *A61M 2205/584* (2013.01); *A61M 2205/587* (2013.01); *A61M 2205/6009* (2013.01)

(58) Field of Classification Search
CPC ............ A61M 5/1409; A61M 5/16831; A61M 2005/16863; A61M 2205/3313; A61M 2205/3569; A61M 2205/502; A61M 2205/584; A61M 2205/587; A61M 2205/6009; H04W 4/80; H04W 4/00; H04W 4/029; A61J 7/0418; A61J 7/04; A61J 7/0409; A61J 7/0076; A61J 7/0463; A61J 2200/30; A61J 2200/74; G06F 19/3462; A61N 1/37518; A61N 1/0551; A61N 1/0558; A61N 1/36062; A61N 1/36185; A61N 1/37223; A61N 1/37229; A61N 1/37247; A61N 1/37252; A61N 1/3756; A61N 1/3787; A61B 5/00; H02J 50/10; H02J 50/20; H02J 50/40; H02J 50/80; H02J 50/90; H02J 7/00034; H02J 2310/23

See application file for complete search history.

(56) References Cited

U.S. PATENT DOCUMENTS

| | | |
|---|---|---|
| 10,857,344 B2 | 12/2020 | Witt |
| 2013/0208497 A1* | 8/2013 | Provost ............... F21V 33/0068 362/555 |
| 2016/0261974 A1 | 9/2016 | Arrizza |
| 2022/0001103 A1* | 1/2022 | Jense .................... A61M 39/10 |

FOREIGN PATENT DOCUMENTS

| | | | |
|---|---|---|---|
| CN | 109036507 A | | 12/2018 |
| JP | 2018512773 A | | 5/2018 |
| JP | 2018113029 A | | 7/2018 |
| WO | 2015116794 A1 | | 8/2015 |
| WO | WO-2016099551 A1 | * | 6/2016 |
| WO | 2016122976 A1 | | 8/2016 |

\* cited by examiner

SYSTEM, METHOD, AND PRODUCT FOR IDENTIFYING A LUMEN

CROSS-REFERENCE TO RELATED APPLICATIONS

This application is the United States national phase of International Application No. PCT/us2020/016546 filed Feb. 4, 2020, and claims priority to U.S. Provisional Application No. 62/800,609, entitled "System, Method, and Product for Identifying a Lumen", filed Feb. 4, 2019. The entire disclosures of which are hereby incorporated by reference.

BACKGROUND

A patient may be connected to multiple lumens or fluid lines (e.g., IV lines, etc.). For example, a patient may be connected to multiple channels of an infusion pump system including a plurality of infusion pumps. As an example, a patient in an emergency room may be connected to ten or more fluid lines at the same time. The multiple fluid lines may result in confusion as to which fluid line at the patient connects to which infusion pump or fluid source. For example, when line maintenance is ordered, a nurse may have to trace a fluid line from a connection of the fluid line at an infusion pump or fluid source to a connection of the fluid line at the patient, or vice-versa. However, when multiple fluid lines are crisscrossed, overlapping, and/or tangled, it may be difficult to identify a correct line for maintenance, infusion, removal, and/or the like.

SUMMARY

Accordingly, provided are improved systems, devices, products, apparatus, and/or methods for identifying a lumen.

According to some non-limiting embodiments or aspects, provided is a system comprising: a plurality of smart devices configured to be connected to a plurality of lumens, wherein each smart device includes a visual indicator, communication circuitry, and a user input component configured to receive a user input from a user; a medication source system including a plurality of medication source devices connected to the plurality of lumens, wherein each medication source device includes a visual indicator, communication circuitry, and a user input component configured to receive a user input from the user, wherein the communication circuitry of a medication source device is configured to establish communication with the communication circuitry of a smart device based on the user input to the user input component of the medication source device and the user input to the user input component of the smart device; and one or more processors programmed and/or configured to: control the visual indicator of the smart device and the visual indicator of the medication source device to produce a same type of visual output based on a communication established between the communication circuitry of the medication source device and the communication circuitry of the smart device; associate the same type of visual output with a same lumen of the plurality of lumens, wherein the medication source device is connected to the same lumen; obtain medication data associated with a first type of medication delivered or scheduled to be delivered via the same lumen to a patient and a second type of medication delivered or scheduled to be delivered via the same lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

In some non-limiting embodiments or aspects, the visual indicator of the smart device includes a light emitting diode, and wherein the same type of visual output is a same color of light.

In some non-limiting embodiments or aspects, the light emitting diode is configured to emit a plurality of different colors of light, and wherein the one or more processors are further programmed and/or configured to: determine a color of the same color of light for the visual indicator of the smart device and the visual indicator of the medication source device to produce based on at least one of the user input to the user input component of the medication source device and the user input to the user input component of the smart device.

In some non-limiting embodiments or aspects, the light emitting diode is configured to emit a plurality of different colors of light, and wherein the one or more processors are further programmed and/or configured to: determine the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

In some non-limiting embodiments or aspects, the medication source system includes an infusion pump system, and wherein the plurality of medication source devices includes a plurality of infusion pumps.

In some non-limiting embodiments or aspects, the first type of medication is delivered via the same lumen to the patient, wherein the second type of medication is scheduled to be delivered via the same lumen to the patient, and wherein the one or more processors are programmed and/or configured to provide the indication of whether the second type of medication is compatible for delivery via the same lumen associated with the same type of visual output by: controlling the medication source device to inhibit or prevent delivery of the second medication via the same lumen associated with the same type of visual output.

In some non-limiting embodiments or aspects, the first type of medication is delivered via the same lumen to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

In some non-limiting embodiments or aspects, the first type of medication and the second type of medication is delivered via the same lumen associated with the same type of visual output to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

In some non-limiting embodiments or aspects, the visual indicator of the smart device is configured to produce the same type of visual output as the visual indicator of the medication source device in response to being connected to a lumen at a same time the communication is established between the communication circuitry of the medication source device and the communication circuitry of the smart device, and wherein the visual indicator of the smart device is configured to automatically stop producing the same type of visual output as the visual indicator of the medication source device in response to being disconnected from the lumen.

In some non-limiting embodiments or aspects, the communication circuitry of another medication source device is configured to establish communication with the communication circuitry of another smart device based on the user input to the user input component of the another medication source device and the user input to the user input component of the another smart device, and wherein the one or more processors are further programmed and/or configured to: control the visual indicator of the another smart device and the visual indicator of the another medication source device to produce another same type of visual output based on the communication established between the communication circuitry of the another medication source device and the communication circuitry of the another smart device, wherein the another same type of visual output is different than the same type of visual output; associate the another same type of visual output with another same lumen of the plurality of lumens, wherein the another medication source device is connected to the another same lumen; obtain medication data associated with a third type of medication delivered or scheduled to be delivered via the another same lumen to the patient; and determine, based on the medication data, a compatibility of the second type of medication for delivery via the another same lumen as the third type of medication, wherein the indication further indicates whether the second type of medication is compatible for delivery via the another same lumen associated with the another same type of visual output.

According to some non-limiting embodiments or aspects, provided is a method comprising: connecting a plurality of smart devices to a plurality of lumens, wherein each smart device includes a visual indicator, communication circuitry, and a user input component, connecting a plurality of medication source devices of a medication source system to the plurality of lumens, wherein each medication source device includes a visual indicator, communication circuitry, and a user input component; receiving, via the user input component of a smart device, user input; receiving, via the user input component of a medication source device, user input; establishing, with the communication circuitry of the smart device and the communication circuitry of the medication source device, a communication between the smart device and the medication source device based on the user input received by the user input component of the medication source device and the user input received by the user input component of the smart device; controlling, with at least one processor, the visual indicator of the smart device and the visual indicator of the medication source device to produce a same type of visual output based on the communication established between the medication source device and the smart device; associating, with at least one processor, the same type of visual output with a same lumen of the plurality of lumens, wherein the medication source device is connected to the same lumen; obtaining, with at least one processor, medication data associated with a first type of medication delivered or scheduled to be delivered via the same lumen to a patient and a second type of medication delivered or scheduled to be delivered via the same lumen to the patient, wherein the first type of medication is different than the second type of medication; determining, with at least one processor, based on the medication data, a compatibility of the second type of medication for delivery via the same lumen as the first type of medication; and providing, with at least one processor, an indication of whether the second type of medication is compatible for delivery via the same lumen associated with the same type of visual output.

In some non-limiting embodiments or aspects, the visual indicator of the smart device includes a light emitting diode, and wherein the same type of visual output is a same color of light.

In some non-limiting embodiments or aspects, the light emitting diode is configured to emit a plurality of different colors of light, and wherein the method further comprises: determining, with at least one processor, a color of the same color of light for the visual indicator of the smart device and the visual indicator of the medication source device to produce based on at least one of the user input received by the user input component of the medication source device and the user input received by the user input component of the smart device.

In some non-limiting embodiments or aspects, the light emitting diode is configured to emit a plurality of different colors of light, and wherein the method further comprises: determining, with at least one processor, the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

In some non-limiting embodiments or aspects, the medication source system includes an infusion pump system, and wherein the plurality of medication source devices includes a plurality of infusion pumps.

In some non-limiting embodiments or aspects, the method further comprises: delivering, with the same lumen associated with the same type of visual output, the first type of medication to the patient, wherein the second type of medication is scheduled to be delivered via the same lumen to the patient, and wherein providing the indication of whether the second type of medication is compatible for delivery via the same lumen associated with the same type of visual output further comprises: controlling the medication source device to inhibit or prevent delivery of the second medication via the same lumen associated with the same type of visual output.

In some non-limiting embodiments or aspects, the method further comprises: delivering, with the same lumen associated with the same type of visual output, the first type of medication to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

In some non-limiting embodiments or aspects, the method further comprises delivering, with the same lumen associated with the same type of visual output, the first type of medication and the second type of medication to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

In some non-limiting embodiments or aspects, the method further comprises: producing, with the visual indicator of the smart device, the same type of visual output as the visual indicator of the medication source device in response to being connected to a lumen at a same time the communication is established between the medication source device and the smart device; and automatically stopping, with the visual indicator of the smart device, production of the same type of visual output as the visual indicator of the medication source device in response to being disconnected from the lumen.

In some non-limiting embodiments or aspects, the method further comprises: receiving, by the user input component of another smart device, user input; receiving, by the user input component of another medication source device, user input; establishing, with the communication circuitry of the another medication source device and the communication circuitry of the another smart device, a communication between the another medication source device and the another smart device based on the user input received by the user input component of the another medication source device and the user input received by the user input component of the another smart device; controlling, with at least one processor, the visual indicator of the another smart device and the visual indicator of the another medication source device to produce another same type of visual output based on the communication established between the another medication source device and the another smart device, wherein the another same type of visual output is different than the same type of visual output; associating, with at least one processor, the another same type of visual output with another same lumen of the plurality of lumens, wherein the another medication source device is connected to the another same lumen; obtaining, with at least one processor, medication data associated with a third type of medication delivered or scheduled to be delivered via the another same lumen to the patient; and determining, with at least one processor, based on the medication data, a compatibility of the second type of medication for delivery via the another same lumen as the third type of medication, wherein the indication further indicates whether the second type of medication is compatible for delivery via the another same lumen associated with the another same type of visual output.

According to some non-limiting embodiments or aspects, provided is a system comprising: one or more processors programmed and/or configured to: control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associate the same type of visual output with the lumen; obtain medication data associated with a first type of medication delivered or scheduled to be delivered via the lumen to a patient and a second type of medication delivered or scheduled to be delivered via the lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

According to some non-limiting embodiments or aspects, provided is a computer-implemented method, comprising: controlling, with at least one processor, a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associating, with at least one processor, the same type of visual output with the lumen; obtaining, with at least one processor, medication data associated with a first type of medication delivered or scheduled to be delivered via the lumen to a patient and a second type of medication delivered or scheduled to be delivered via the lumen to the patient, wherein the first type of medication is different than the second type of medication; determining, with at least one processor, based on the medication data, a compatibility of the second type of medication for delivery via the same lumen as the first type of medication; and providing, with at least one processor, an indication of whether the second type of medication is compatible for delivery via the same lumen associated with the same type of visual output.

According to some non-limiting embodiments or aspects, provided is a computer program product comprising at least one non-transitory computer-readable medium including program instructions that, when executed by at least one processor, cause the at least one processor to: control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associate the same type of visual output with the lumen; obtain medication data associated with a first type of medication delivered or scheduled to be delivered via the lumen to a patient and a second type of medication delivered or scheduled to be delivered via the lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

Further non-limiting embodiments or aspects are set forth in the following numbered clauses:

Clause 1. A system comprising: a plurality of smart devices configured to be connected to a plurality of lumens, wherein each smart device includes a visual indicator, communication circuitry, and a user input component configured to receive a user input from a user; a medication source system including a plurality of medication source devices connected to the plurality of lumens, wherein each medication source device includes a visual indicator, communication circuitry, and a user input component configured to receive a user input from the user, wherein the communication circuitry of a medication source device is configured to establish communication with the communication circuitry of a smart device based on the user input to the user input component of the medication source device and the user input to the user input component of the smart device;

and one or more processors programmed and/or configured to: control the visual indicator of the smart device and the visual indicator of the medication source device to produce a same type of visual output based on a communication established between the communication circuitry of the medication source device and the communication circuitry of the smart device; associate the same type of visual output with a same lumen of the plurality of lumens, wherein the medication source device is connected to the same lumen; obtain medication data associated with a first type of medication delivered or scheduled to be delivered via the same lumen to a patient and a second type of medication delivered or scheduled to be delivered via the same lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

Clause 2. The system of clause 1, wherein the visual indicator of the smart device includes a light emitting diode, and wherein the same type of visual output is a same color of light.

Clause 3. The system of any of clauses 1 and 2, wherein the light emitting diode is configured to emit a plurality of different colors of light, and wherein the one or more processors are further programmed and/or configured to: determine a color of the same color of light for the visual indicator of the smart device and the visual indicator of the medication source device to produce based on at least one of the user input to the user input component of the medication source device and the user input to the user input component of the smart device.

Clause 4. The system of any of clauses 1-3, wherein the light emitting diode is configured to emit a plurality of different colors of light, and wherein the one or more processors are further programmed and/or configured to: determine the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

Clause 5. The system of any of clauses 1-4, wherein the medication source system includes an infusion pump system, and wherein the plurality of medication source devices includes a plurality of infusion pumps.

Clause 6. The system of any of clauses 1-5, wherein the first type of medication is delivered via the same lumen to the patient, wherein the second type of medication is scheduled to be delivered via the same lumen to the patient, and wherein the one or more processors are programmed and/or configured to provide the indication of whether the second type of medication is compatible for delivery via the same lumen associated with the same type of visual output by: controlling the medication source device to inhibit or prevent delivery of the second medication via the same lumen associated with the same type of visual output.

Clause 7. The system of any of clauses 1-6, wherein the first type of medication is delivered via the same lumen to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

Clause 8. The system of any of clauses 1-7, wherein the first type of medication and the second type of medication is delivered via the same lumen associated with the same type of visual output to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

Clause 9. The system of any of clauses 1-8, wherein the visual indicator of the smart device is configured to produce the same type of visual output as the visual indicator of the medication source device in response to being connected to a lumen at a same time the communication is established between the communication circuitry of the medication source device and the communication circuitry of the smart device, and wherein the visual indicator of the smart device is configured to automatically stop producing the same type of visual output as the visual indicator of the medication source device in response to being disconnected from the lumen.

Clause 10. The system of any of clauses 1-9, wherein the communication circuitry of another medication source device is configured to establish communication with the communication circuitry of another smart device based on the user input to the user input component of the another medication source device and the user input to the user input component of the another smart device, and wherein the one or more processors are further programmed and/or configured to: control the visual indicator of the another smart device and the visual indicator of the another medication source device to produce another same type of visual output based on the communication established between the communication circuitry of the another medication source device and the communication circuitry of the another smart device, wherein the another same type of visual output is different than the same type of visual output; associate the another same type of visual output with another same lumen of the plurality of lumens, wherein the another medication source device is connected to the another same lumen; obtain medication data associated with a third type of medication delivered or scheduled to be delivered via the another same lumen to the patient; and determine, based on the medication data, a compatibility of the second type of medication for delivery via the another same lumen as the third type of medication, wherein the indication further indicates whether the second type of medication is compatible for delivery via the another same lumen associated with the another same type of visual output.

Clause 11. A method, comprising: connecting a plurality of smart devices to a plurality of lumens, wherein each smart device includes a visual indicator, communication circuitry, and a user input component, connecting a plurality of medication source devices of a medication source system to the plurality of lumens, wherein each medication source device includes a visual indicator, communication circuitry, and a user input component; receiving, via the user input component of a smart device, user input; receiving, via the user input component of a medication source device, user input; establishing, with the communication circuitry of the smart device and the communication circuitry of the medication source device, a communication between the smart device and the medication source device based on the user input received by the user input component of the medication source device and the user input received by the user input component of the smart device; controlling, with at least one processor, the visual indicator of the smart device and the visual indicator of the medication source device to produce a same type of visual output based on the communication established between the medication source device and the smart device; associating, with at least one processor, the same type of visual output with a same lumen of the plurality of lumens, wherein the medication source device is connected to the same lumen; obtaining, with at least one processor, medication data associated with a first type of medication delivered or scheduled to be delivered via the same lumen to a patient and a second type of medication delivered or scheduled to be delivered via the same lumen to the patient, wherein the first type of medication is different than the second type of medication; determining, with at least one processor, based on the medication data, a compatibility of the second type of medication for delivery via the same lumen as the first type of medication; and providing, with at least one processor, an indication of whether the second type of medication is compatible for delivery via the same lumen associated with the same type of visual output.

Clause 12. The method of clause 11, wherein the visual indicator of the smart device includes a light emitting diode, and wherein the same type of visual output is a same color of light.

Clause 13. The method of any of clauses 11 and 12, wherein the light emitting diode is configured to emit a plurality of different colors of light, and wherein the method further comprises: determining, with at least one processor, a color of the same color of light for the visual indicator of the smart device and the visual indicator of the medication source device to produce based on at least one of the user input received by the user input component of the medication source device and the user input received by the user input component of the smart device.

Clause 14. The method of any of clauses 11-13 wherein the light emitting diode is configured to emit a plurality of different colors of light, and wherein the method further comprises: determining, with at least one processor, the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

Clause 15. The method of any of clauses 11-14, wherein the medication source system includes an infusion pump system, and wherein the plurality of medication source devices includes a plurality of infusion pumps.

Clause 16. The method of any of clauses 11-15, further comprising: delivering, with the same lumen associated with the same type of visual output, the first type of medication to the patient, wherein the second type of medication is scheduled to be delivered via the same lumen to the patient, and wherein providing the indication of whether the second type of medication is compatible for delivery via the same lumen associated with the same type of visual output further comprises: controlling the medication source device to inhibit or prevent delivery of the second medication via the same lumen associated with the same type of visual output.

Clause 17. The method of any of clauses 11-17, further comprising: delivering, with the same lumen associated with the same type of visual output, the first type of medication to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

Clause 18. The method of any of clauses 11-17, further comprising: delivering, with the same lumen associated with the same type of visual output, the first type of medication and the second type of medication to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

Clause 19. The method of any of clauses 11-18, further comprising: producing, with the visual indicator of the smart device, the same type of visual output as the visual indicator of the medication source device in response to being connected to a lumen at a same time the communication is established between the medication source device and the smart device; and automatically stopping, with the visual indicator of the smart device, production of the same type of visual output as the visual indicator of the medication source device in response to being disconnected from the lumen.

Clause 20. The method of any of clauses 11-20, further comprising: receiving, by the user input component of another smart device, user input; receiving, by the user input component of another medication source device, user input; establishing, with the communication circuitry of the another medication source device and the communication circuitry of the another smart device, a communication between the another medication source device and the another smart device based on the user input received by the user input component of the another medication source device and the user input received by the user input component of the another smart device; controlling, with at least one processor, the visual indicator of the another smart device and the visual indicator of the another medication source device to produce another same type of visual output based on the communication established between the another medication source device and the another smart device, wherein the another same type of visual output is different than the same type of visual output; associating, with at least one processor, the another same type of visual output with another same lumen of the plurality of lumens, wherein the another medication source device is connected to the another same lumen; obtaining, with at least one processor, medication data associated with a third type of medication delivered or scheduled to be delivered via the another same lumen to the patient; and determining, with at least one processor, based on the medication data, a compatibility of the second type of medication for delivery via the another same lumen as the third type of medication, wherein the indication further indicates whether the second type of medication is compatible for delivery via the another same lumen associated with the another same type of visual output.

Clause 21. A system, comprising: one or more processors programmed and/or configured to: control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associate the same type of visual output with the lumen; obtain medication data associated with a first type of medication delivered or scheduled to be delivered via the lumen to a patient and a second type of medication delivered or scheduled to be delivered via the lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

Clause 22. A computer-implemented method, comprising: controlling, with at least one processor, a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associating, with at least one processor, the same type of visual output with the lumen; obtaining, with at least one processor, medication data associated with a first type of medication delivered or scheduled to be delivered via the lumen to a patient and a second type of medication delivered or scheduled to be delivered via the lumen to the patient, wherein the first type of medication is different than the second type of medication; determining, with at least one processor, based on the medication data, a compatibility of the second type of medication for delivery via the same lumen as the first type of medication; and providing, with at least one processor, an indication of whether the second type of medication is compatible for delivery via the same lumen associated with the same type of visual output.

Clause 23. A computer program product comprising at least one non-transitory computer-readable medium including program instructions that, when executed by at least one processor, cause the at least one processor to: control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen; associate the same type of visual output with the lumen; obtain medication data associated with a first type of medication delivered or scheduled to be delivered via the lumen to a patient and a second type of medication delivered or scheduled to be delivered via the lumen to the patient, wherein the first type of medication is different than the second type of medication; determine, based on the medication data, a compatibility of the second type of medication for delivery via the same lumen as the first type of medication; and provide an indication of whether the second type of medication is compatible for delivery via the same lumen associated with the same type of visual output.

DETAILED DESCRIPTION

Figure 1:
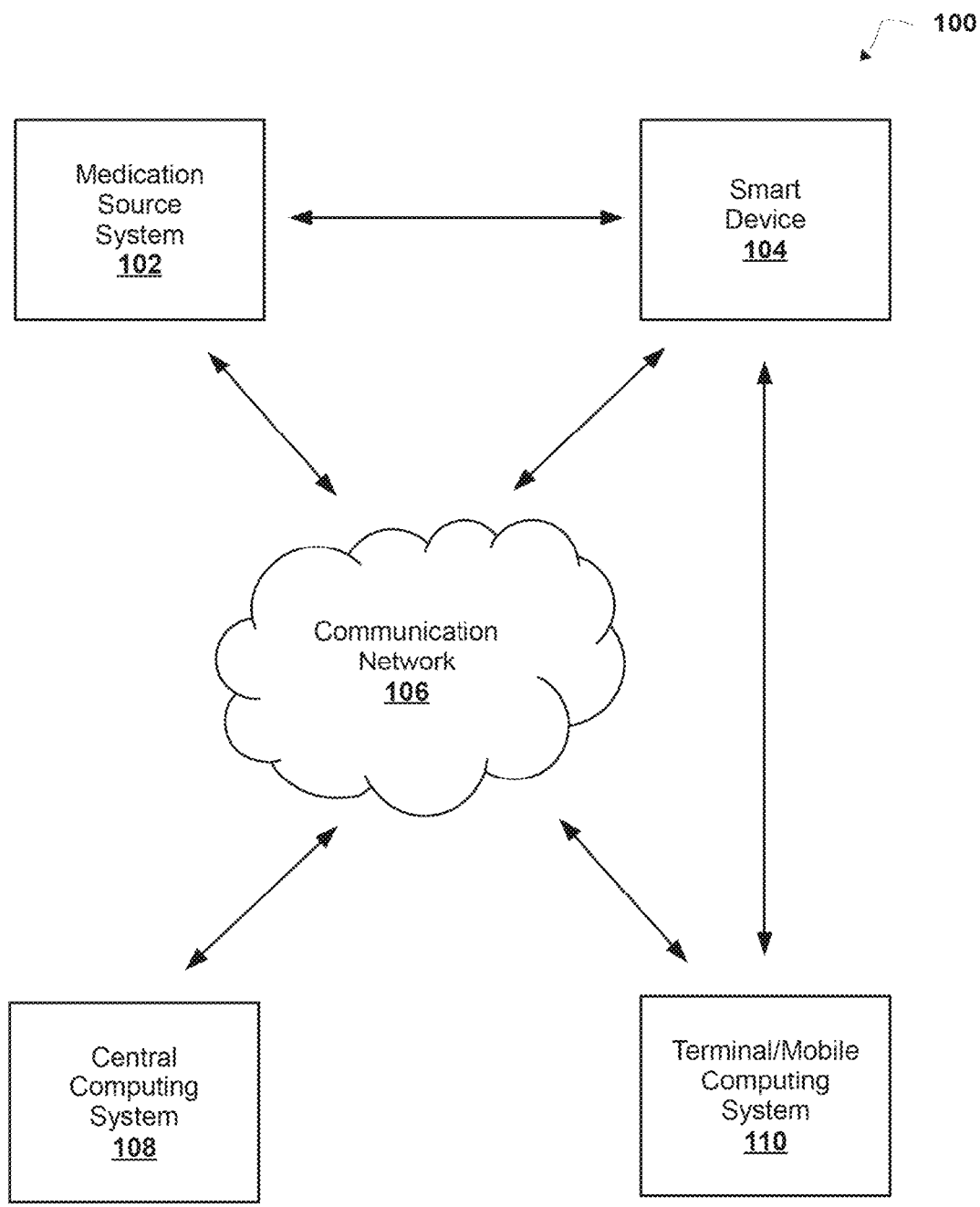
FIG. 1 is a diagram of non-limiting embodiments or aspects of an environment in which systems, devices, products, apparatus, and/or methods, described herein, can be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices directly or indirectly communicating in the network environment may constitute a "system" or a "computing system".

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Provided are improved systems, devices, products, apparatus, and/or methods for identifying a lumen. Existing systems for identifying a lumen may use tape, labels, hand-written nodes, and/or LED lights to identify a lumen. However, existing systems for identifying a lumen may not automatically associate an identified lumen with a fluid pump or fluid source connected to the identified lumen and/or with medication data associated with one or more medications delivered and/or scheduled to be delivered via the identified lumen. In this way, existing systems for identifying a lumen have no mechanism to automatically determine a compatibility of medications delivered and/or scheduled to be delivered via a same lumen and/or to inhibit or prevent delivery of incompatible medications via the same lumen. Accordingly, existing systems for identifying a lumen may not sufficiently reduce or eliminate IV line complexity and/or medication delivery errors and/or sufficiently improve compliance with lumen maintenance procedures (e.g., line flushing, etc.).

Non-limiting embodiments or aspects of the present disclosure are directed to systems, devices, products, apparatus, and/or methods that automatically associate an identified lumen with a fluid pump or fluid source connected to the identified lumen and/or with medication data associated with one or more medications delivered and/or scheduled to be delivered via the identified lumen. For example, a method may include controlling a visual indicator of a smart device and a visual indicator of a medication source device to produce a same type of visual output based on a communication established between communication circuitry of the medication source device and communication circuitry of the smart device, the medication source device being connected to a lumen, and the smart device being configured to be connected to the lumen; associating the same type of visual output with the lumen; obtaining medication data associated with a first type of medication delivered or scheduled to be delivered via the lumen to a patient and a second type of medication delivered or scheduled to be delivered via the lumen to the patient, the first type of medication being different than the second type of medication; determining, based on the medication data, a compatibility of the second type of medication for delivery via the same lumen as the first type of medication; and providing an indication of whether the second type of medication is compatible for delivery via the same lumen associated with the same type of visual output.

In this way, non-limiting embodiments or aspects of the present disclosure provide for automatically determining a compatibility of medications delivered and/or scheduled to be delivered via a same lumen and/or inhibiting or preventing delivery of incompatible medications via the same lumen, which may enable improved reduction or elimination of IV line complexity and/or medication delivery errors and/or improved compliance with lumen maintenance procedures (e.g., line flushing, etc.).

Referring now to FIG. 1, FIG. 1 is a diagram of an example environment 100 in which devices, systems, methods, and/or products described herein, may be implemented. As shown in FIG. 1, environment 100 includes medication source system 102, smart device 104, communication network 106, central computing system 108, and terminal/mobile computing system 110. Systems and/or devices of environment 100 can interconnect via wired connections, wireless connections, or a combination of wired and wireless connections.

In some non-limiting embodiments or aspects, medication source system 102 includes one or more devices capable of delivering one or more fluids to one or more lumens (e.g., fluid lines, IV lines, etc.). For example, medication source system 102 may include one or more manual fluid delivery systems (e.g., one or more IV bags, one or more syringes, etc.) and/or an infusion pump system including one or more infusion pumps. In some non-limiting embodiments, smart device 104 may include a plurality of smart devices 104 (e.g., one or more other and/or differ types of smart devices 104, etc.).

In some non-limiting embodiments or aspects, medication source system 102 includes one or more devices capable of receiving information and/or data from smart device 104, communication network 106, central computing system 108, and/or terminal/mobile computing system 110 and/or communicating information and/or data to smart device 104, communication network 106, central computing system 108, and/or terminal/mobile computing system 110. For example, medication source system 102 may include one or more computing systems including one or more processors (e.g., one or more computing devices, one or more mobile computing devices, etc.).

Further details regarding non-limiting embodiments or aspects of medication source system 102 are provided below with regard to FIGS. 2A, 2C, and 3.

In some non-limiting embodiments or aspects, smart device 104 includes one or more devices capable of receiving information and/or data from medication source system 102, one or more other smart devices 104, communication network 106, central computing system 108, and/or terminal/mobile computing system 110 and/or communicating information and/or data to medication source system 102, one or more other smart devices 104, communication network 106, central computing system 108, and/or terminal/mobile computing system 110. For example, smart device 104 may include one or more computing systems including one or more processors (e.g., one or more computing devices, one or more mobile computing devices, etc.). In some non-limiting embodiments or aspects, smart device 104 may be capable of receiving information (e.g., from medication source system 102 (e.g., from medication source controller 204 and/or from medication source device 206, etc.), from terminal/mobile computing system 110, from one or more other smart devices 104, etc.) via a short range wireless communication connection (e.g., an NFC communication connection, an RFID communication connection, a Bluetooth® communication connection, and/or the like), and/or communicating information (e.g., to medication source system 102 (e.g., to medication source controller 204 and/or to medication source device 206, etc.), to terminal/mobile computing system 110, to one or more other smart devices 104, etc.) via a short range wireless communication connection.

Figure 6A:
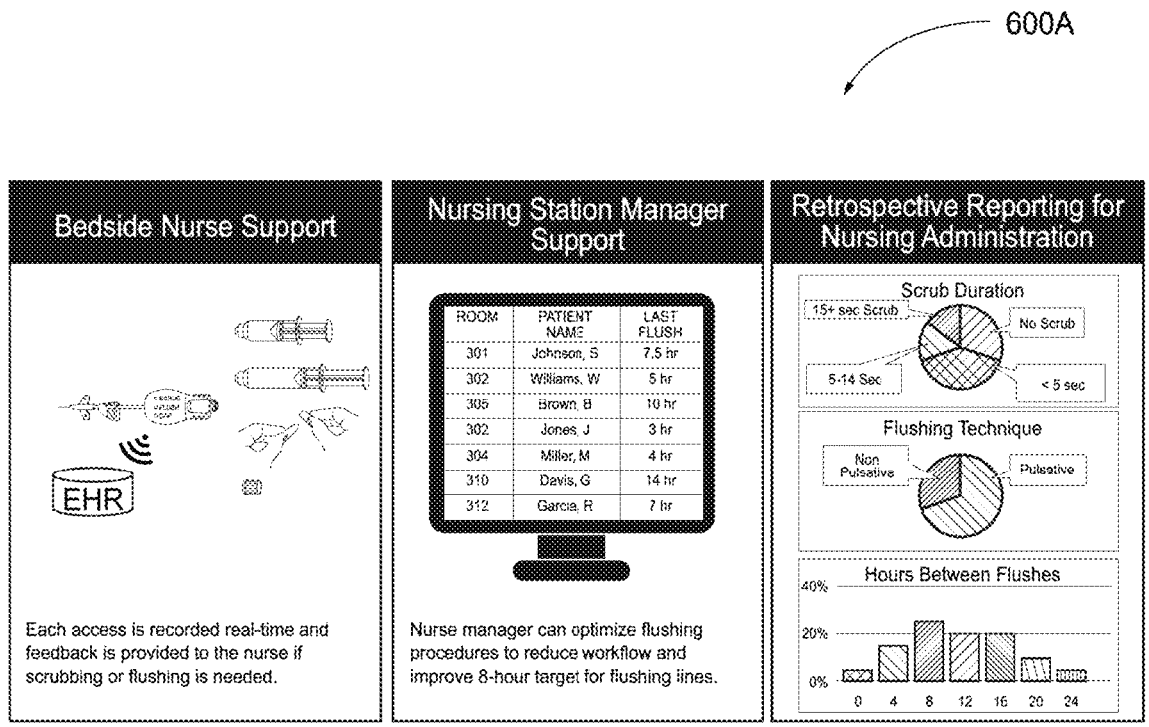
FIGS. 6A and 6B show non-limiting embodiments or aspects of output of one or more systems and/or one or more devices of FIG. 1.
Figure 6B:
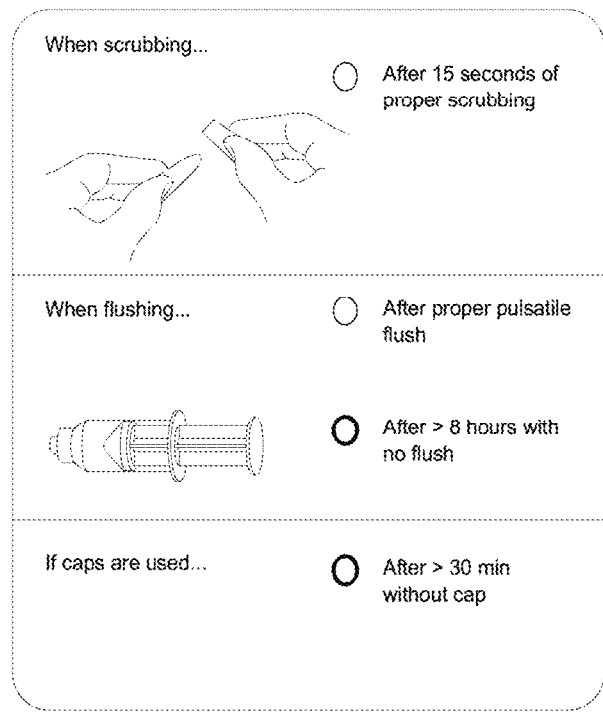

In some non-limiting embodiments or aspects, as shown in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, and/or a detected connection or capping event (e.g., with processor 304, memory 306, storage component 308, input component 310, output component 312, etc.) to store events and report compliance performance for compliance event monitoring.

Further details regarding non-limiting embodiments or aspects of smart device 104 are provided below with regard to FIGS. 2A-2C, 3, 4A-4C, 5A-5C, 6A, 6B, and 7.

In some non-limiting embodiments or aspects, communication network 106 includes one or more wired and/or wireless networks. For example, communication network 106 includes a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or any combination of these or other types of networks.

In some non-limiting embodiments or aspects, central computing system 108 includes one or more devices capable of receiving information and/or data from medication source system 102, smart device 104, communication network 106, and/or terminal/mobile computing system 110 and/or communicating information and/or data to medication source system 102, smart device 104, communication network 106, and/or terminal/mobile computing system 110. For example, medication source system 102 may include one or more computing systems including one or more processors (e.g., one or more computing devices, one or more mobile computing devices, etc.). In some non-limiting embodiments or aspects, central computing system 108 includes a secure hospital server and/or one or more secure hospital databases that store personally identifiable information (PII) and/or Health Insurance Portability and Accountability Act (HIPAA) protected information.

In some non-limiting embodiments or aspects, terminal/mobile computing system 110 includes one or more devices capable of receiving information and/or data from medication source system 102, smart device 104, communication network 106, and/or central computing system 108 and/or communicating information and/or data to medication source system 102, smart device 104, communication network 106, and/or central computing system 108. For example, terminal/mobile computing system 110 may include one or more computing systems including one or more processors (e.g., one or more computing devices, one or more mobile computing devices, etc.). In some non-limiting embodiments or aspects, terminal/mobile computing system 110 includes a nurse station in a hospital. For example, as shown in an implementation 600A FIG. 6A, terminal/mobile computing system 110 may provide bedside nurse support (e.g., recordation of each access to needleless connector 214 and/or lumen 212 in real-time and feedback to a nurse if scrubbing or flushing is determined to be due or needed according to the recorded access, etc.), nursing station manager support (e.g., optimization of flushing procedures to reduce workflow and improve timed targets for flushing a needleless connector 214 and/or lumen 212, etc.), retrospective reporting for nursing administration (e.g., a scrub duration, a flushing technique, a time between flushes, and/or the like for a needleless connector 214 and/or lumen 212, etc.), and/or the like.

Figure 2A:
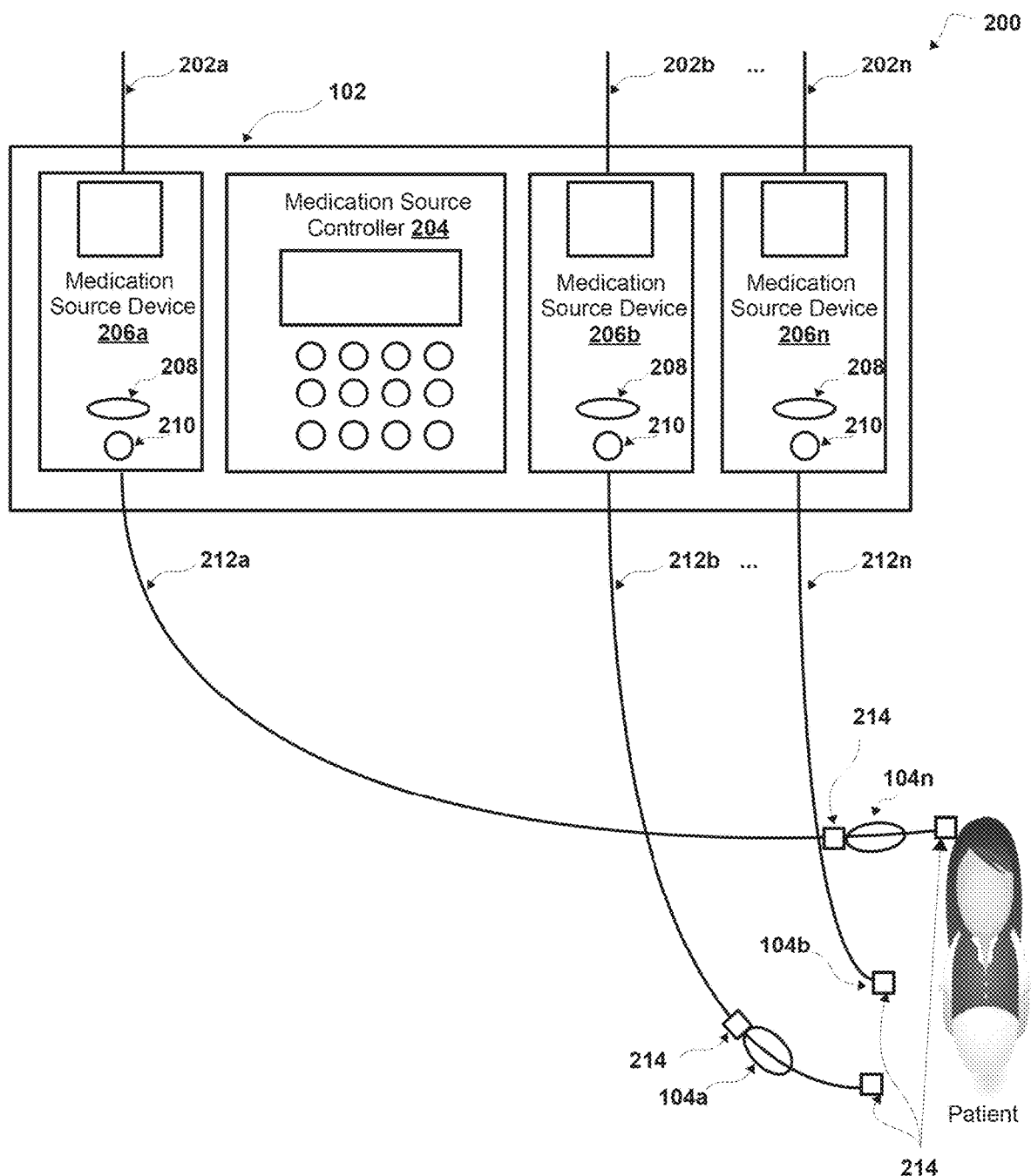
FIGS. 2A-2C are diagrams of non-limiting embodiments or aspects of an implementation of one or more systems and/or one or more devices of FIG. 1.
Figure 2B:
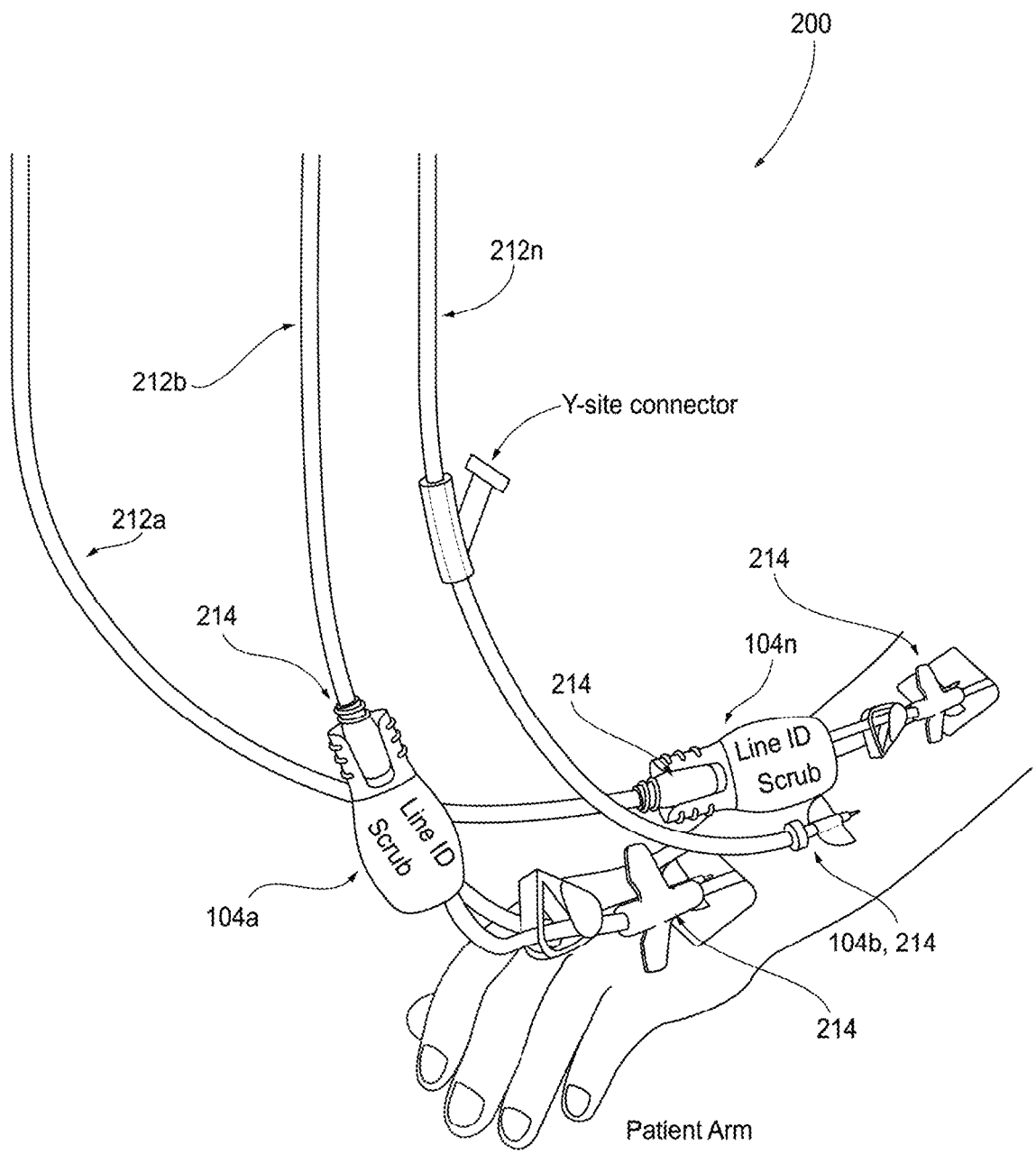
Figure 2C:
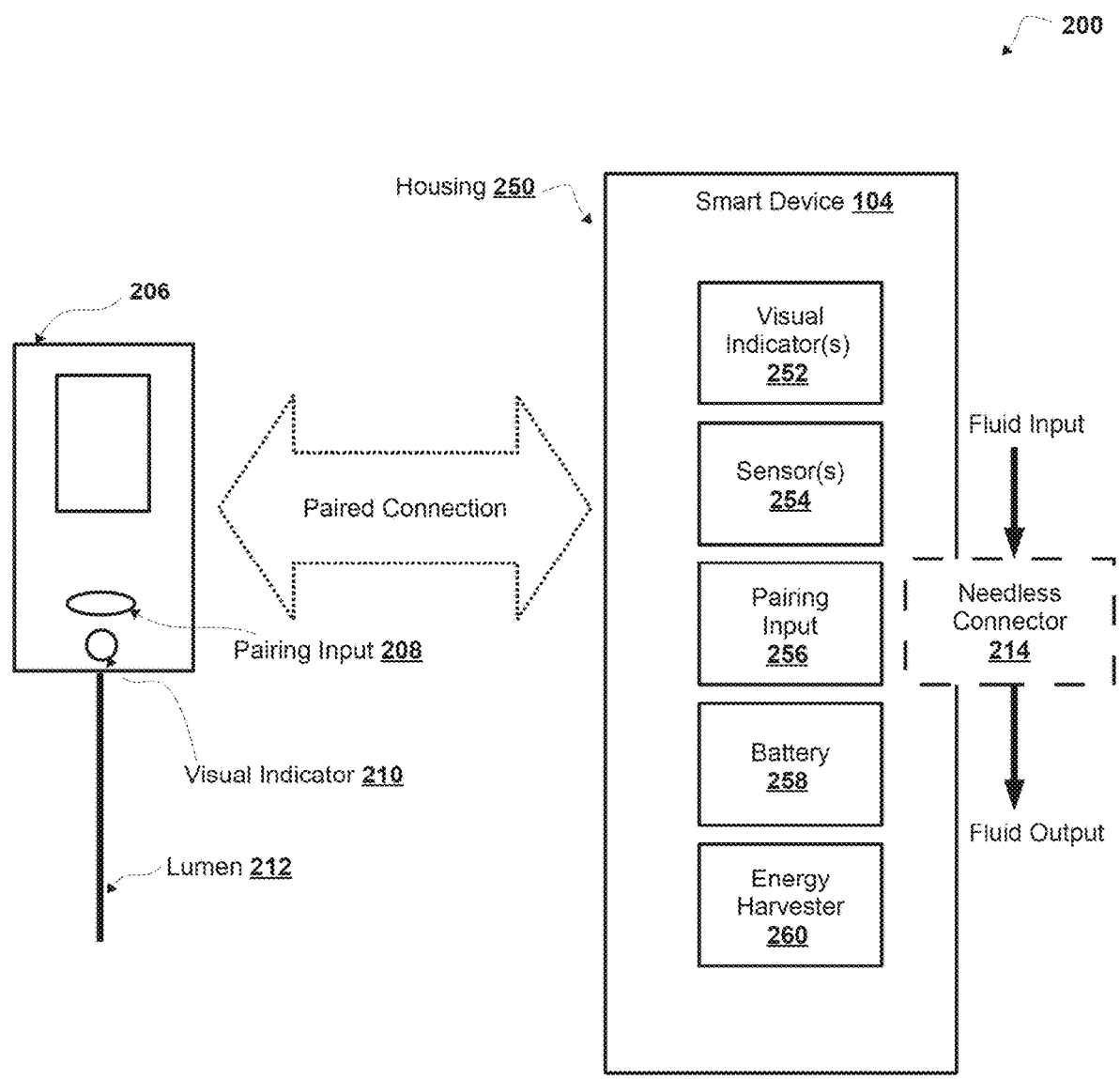

Referring now to FIGS. 2A-2C, FIGS. 2A-2C are diagrams of non-limiting embodiments or aspects of an implementation 200 of one or more systems and/or one or more devices of FIG. 1. As shown in FIGS. 2A and 2C, medication source system 102 may include a medication source controller 204 and/or one or more medication source devices 206 (e.g., a plurality of mediation source devices 206a, 206b, . . . 206n, etc.). As an example, medication source controller 204 may include an infusion pump controller and/or medication source device 206 may include an infusion pump. In such an example, medication source system 102 may include the BD Alaris™ system. For example, medication source system 102 may include a BD Alaris™ PC Unit and one or more BD Alaris™ Pump Modules. As another example, medication source controller 204 may include a bed-side console or computing device, which may be separate from an infusion pump system, and/or medication source device 206, which may be separate from an infusion pump, may be associated with and/or connected to a medication source (e.g., an IV bag, a syringe, an end of an IV line connected and proximal to an IV bag or a syringe, etc.).

As shown in FIG. 2A, the plurality of medication source devices 206a, 206b, . . . 206n may be connected to a plurality of lumens (e.g., fluid lines, etc.) 202a, 202b, . . . 202n (e.g., for receiving a fluid and/or a medication at medication source system 102) and/or a plurality of lumens (e.g., fluid lines, etc.) 212a, 212b, 212n (e.g., for delivering a fluid and/or a medication from medication source system 102, etc.). As shown in FIG. 2C, medication source device 206 may include pairing input 208 (e.g., a button, input component 310, etc.) and/or visual indicator 210 (e.g., a multi-color LED(s), output component 312, etc.). As shown in FIGS. 2A and 2B, the plurality of lumens 212a, 212b, . . . 212n may be connected to a plurality of smart devices 104a, 104b, . . . 104n.

However, non-limiting embodiments or aspects are not limited thereto and a patient may be connected to only a single lumen, and the lumen may (or may not) be connected to any medication source device 206 and/or fluid source. For example, if a patient is connected to a single lumen, a smart device 104 may be connected to the single lumen, and the smart device 104 may be associated with a particular color associated with that lumen. A doctor and/or a pharmacy may issue an order for a type of medication to be delivered to the patient, and the order for the type of medication can link the color of the lumen to the order to reduce or avoid medication delivery errors. As an example, a first patient may have a "pink" LED light illuminated on smart device 104, and an order from a doctor and/or a pharmacy that includes a new type of medication or therapy to be delivered and instructions for a user (e.g., a nurse, etc.) to deliver the new type of medication on the one and only "pink" line to implement an error checking process. When the user (e.g., the nurse, etc.) initiates delivery of the medication to the patient, the user can ensure that 104 smart device is emitting the pink color for an additional safety check to ensure that the user has the right patient for the right type of medication. If smart device 104 is emitting a color of light other than the "pink" light (e.g., a "green" light or a "blue" light) and the order for the medication indicates a that the medication should only be delivered via a "pink" colored lumen, the user (e.g., the nurse, etc.) may initiation of delivery to the patient (e.g., not deliver the medication to the patient, etc.) because the user can determine that the order and the color does not match, which indicates that there may be an issue and/or an incompatibility with medication for the patient and/or the lumen. For example, li the patient is connected to a single lumen, the order can indicate to deliver give saline on the "pink" line and to deliver antibiotics on the same "pink" line, etc. However, if there is a drug incompatibility ordered, the order can alter the user that additional flushing is indicated for the "pink" line to ensure that the pink line properly flushed before subsequent medications that may be incompatible with medications or fluids previously delivered via the "pink" line are delivered. As an example, if there are two lumens connected to a single patient (e.g., a single "pink" line and a single "blue" line) an order may indicate to deliver saline via the "pink" lumen or line and deliver antibiotics via the "blue" lumen or line, and/or the like. Accordingly, in some non-limiting embodiments or aspects, smart device 104 may simply be used for proper patient lumen identification and/or to direct a user to use an optimal lumen for delivery of a fluid to the patient, which may ensure the proper therapy is delivered to the optimal or proper lumen, thereby reducing scenarios associated with a wrong dose, a wrong patient, a wrong lumen, and/or the like with smart device 104.

In some non-limiting embodiments or aspects, smart device 104 is configured to be removably connected to needleless connector 214 and/or a portion of lumen 212 proximate needleless connector 214, such as an IV lumen (e.g., a peripherally inserted central catheter (PICC), a peripheral intravenous catheter (PIVC), a central venous catheter (CVC), etc.), and/or the like. For example, smart device 104 may include a clamp, an adhesive, or other attachment means configured to removably connect smart device 104 to needleless connector 214 and/or lumen 212 proximate needleless connector 214. As an example, as shown in FIGS. 2A and 2B, smart device 104a may be connected to needleless connector 214 and/or a catheter lumen that connects a catheter to lumen 212b, and/or smart device 104n may be connected to needleless connector 214 and/or a catheter lumen that connects a catheter to lumen 212a. In some non-limiting embodiments or aspects, smart device 104 includes needleless connector 214. For example, smart device 104 may be integrated with needleless connector 214 (e.g., within a needleless connector 214 and/or within a catheter hub of a needleless connector of a fluid invasive device, etc.). As an example, as shown in FIGS. 2A and 2B, smart device 104b may include needleless connector 214 and/or a catheter hub that connects a catheter lumen to lumen 212n via a Y-site connector. In such an example, smart device 104 may include needleless connector 214 including housing 402 of needleless connector 214 within housing 250 (e.g., integrated with housing 250, encompassed within housing 250, etc.).

Figure 4A:
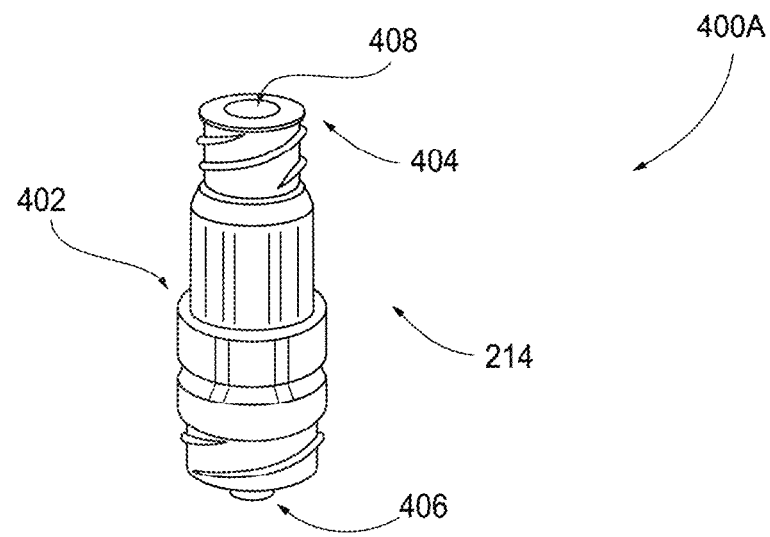
FIG. 4A is a side view of non-limiting embodiments or aspects of an implementation of a needleless connector.
Figure 4B:
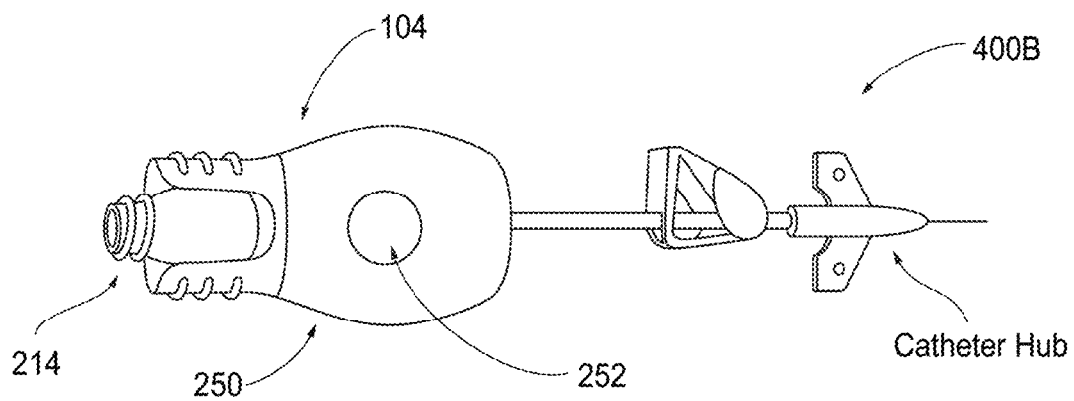
FIG. 4B is a side view of non-limiting embodiments or aspects of an implementation of a smart device and a needleless connector.
Figure 4C:
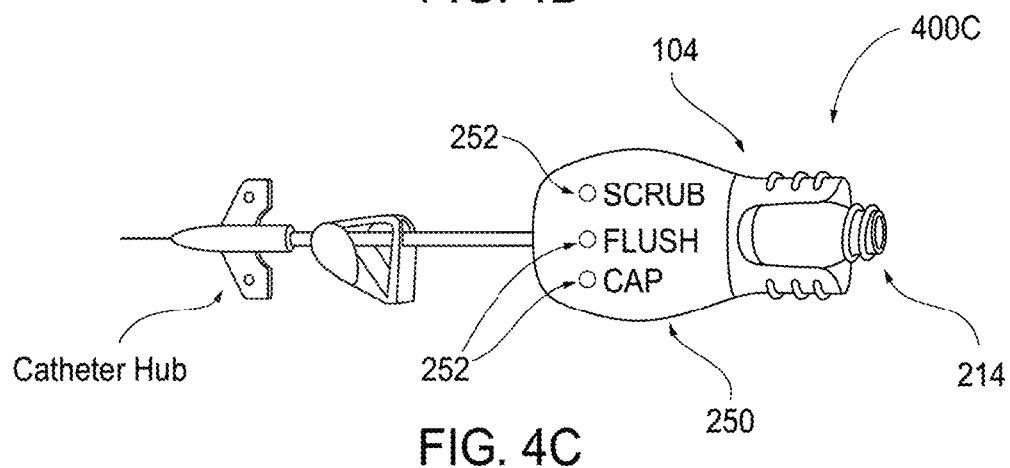
FIG. 4C is a side view of non-limiting embodiments or aspects of an implementation of a smart device and a needleless connector.

Referring also to FIG. 4A, FIG. 4A is a side view of non-limiting embodiments or aspects of an implementation 400A of a needleless connector 214. As shown in FIG. 4A, a needleless connector 214 may include a fluid flow path in a housing 402 between an inlet 404 and an outlet 406 opposite the inlet 404. Inlet 404 may be fluidically sealed by a displaceable septum 408 configured to be displaced to open or connect inlet 404 to the fluid flow path in response to connection of needleless connector 214 to a medical device (e.g., an infusion pump, an IV bag, a syringe, an IV line, etc.). For example, the needleless connector 214 may include the BD MaxPlus™ connector, the BD MaxZero™ needle-free connector, and/or the like. However, non-limiting embodiments or aspects are not limited thereto, and the needleless connector 214 may include any needleless connector 214 for use in fluid administration. In some non-limiting embodiments or aspects, one or more components of smart device 104 may be included within housing 402 of needleless connector 214. For example, housing 402 of needleless connector 214 may include housing 250 of smart device 104 (e.g., housing 250 may be integrated with housing 402, encompassed within housing 402, etc.).

As shown in FIG. 2C, smart device 104 may include visual indicator 252 (e.g., one or more visual indictors, a plurality of visual indicators, a multi-color LED(s), a plurality of LEDs, output component 312, etc.), sensor 254 (e.g., one or more sensors, a plurality of sensors, a sensor suite, etc.), pairing input 256 (e.g., one or more buttons, one or more force sensor, one or more accelerometers, input component 310, etc.), battery 258, and/or energy harvester 260 (e.g., a thermoelectric energy harvester, a photovoltaic energy harvester, a piezoelectric energy harvester, etc.). Visual indicator 252, sensor 254, pairing input 256, battery 258, energy harvester 260 and all or a portion of needleless connector 214 may be included within housing 250 of smart device 104. Visual indicator 252 may be visible through and/or extend from a sidewall of housing 250. Battery 258 and/or energy harvester 260 may provide power for operating components of smart device 104, such as visual indicator 252, sensor 254, pairing input 256, a rechargeable battery of battery 258, one or more components of device 300 included in smart device 104, and/or the like.

In some non-limiting embodiments or aspects, smart device 104 may include a label (e.g., a human readable label, etc.) that characterizes visual indicator 252 of smart device 104. For example, as shown in implementation 400C in FIG. 4C, smart device 104 may include labels associated with visual indicators 252 (e.g., on a sidewall of housing 250, etc.) that characterize each visual indicator 252 as configured for providing an indication associated a particular event, such as one of: a scrubbing event in which needleless connector 214 is scrubbed with a disinfectant (e.g., a label "SCRUB", etc.); a flushing event in which needleless connector 214 is flushed with a solution (e.g., a label "FLUSH", etc.); a connection or capping event in which needleless connector 214 is connected to a medical device (e.g., a label "CAP", etc.); and/or the like. In some non-limiting embodiments or aspects, smart device 104 may include a single visual indicator 252 (e.g., as shown in implementation 400B in FIG. 4B). For example, smart device 104 may control single visual indicator 252 to illuminate in a particular color and/or in a particular pattern to provide an indication or prompt to a user, such as to illuminate a continuous green in response to sensing that scrubbing of needleless connector 214 has occurred for a predetermined period of time (e.g., 15 seconds, etc.), to illuminate a pulsating green in response to sensing that a proper pulsatile flush has occurred, to illuminate a pulsating red in response to determining that a pulsatile flush of needleless connector 214 has not occurred for a predetermined period of time (e.g., 88 hours, etc.), to illuminate a continuous red in response to determining that needleless connector 214 has not been capped with a disinfectant cap for a predetermined period of time (e.g., over minutes, etc.)

In some non-limiting embodiments or aspects, communication circuitry (e.g., communication interface 314, etc.) of medication source device 206 is configured to establish communication with communication circuitry (e.g., communication interface 314, etc.) of smart device 104 based on user input to pairing input 208 of medication source device 206 and user input to pairing input 256 of smart device 104. For example, medication source device 206 may establish a short range wireless communication connection (e.g., an NFC communication connection, an RFID communication connection, a Bluetooth® communication connection, etc.) with smart device 104. As an example, visual indicator 210 may be configured to emit a predetermined light pattern (e.g., to blink rapidly to indicate that medication source device 206 is in a pairing mode, etc.) in response to a predetermined user input to pairing input 208 (e.g., in response to a user pressing and holding a button of pairing input 208, etc.) of medication source device 206. In such an example, smart device 104 may be configured to establish communication with medication source device 206 (e.g., pair and/or activate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

In some non-limiting embodiments or aspects, when medication source device 206 is paired with smart device 104, visual indicator 210 of medication source device 206 and visual indicator 252 of smart device 104 are configured to provide a same type of visual output (e.g., a same color of light from a multi-colored LED, a same pattern of light, etc.). For example, and referring again to FIG. 2A, medication source device 206a may be paired with smart device 104n and each of medication source device 206a and smart device 104n may output a first color of light (e.g., red light), medication source device 206b may be paired with smart device 104a and each of medication source device 206b and smart device 104a may output a second color of light (e.g., green light), medication source device 206n may be paired with smart device 104b and each of medication source device 206n and smart device 104b may output a third color of light (e.g., blue light), and/or the like.

In some non-limiting embodiments or aspects, sensor 254 includes at least one of: one or more force sensors (e.g., one or more piezoelectric elements or transducers, one or more force sensitive resistive (FSR) sensors, one or more strain gauges, etc.); one or more pressure sensors; one or more acoustic sensors; one or more optical sensors (e.g., an optical sensor configured to detect at least one of a color signature and a reflectance of a medical device connected to smart device 104, etc.), one or more identification sensors (e.g., an identification sensor configured to detect an identification tag on a medical device connected to or being connected to the needleless connector 214, such as a magnetometer configured to detect a magnetic material, a barcode scanner configured to read a bar code, etc.); one or more position sensors (e.g., a position sensor configured to detect movement of smart device 104, etc.); one or more RBG color sensors; or any combination thereof.

The number and arrangement of systems, devices, and networks shown in FIGS. 1 and 2A-2C are provided as an example. There can be additional systems, devices and/or networks, fewer systems, devices, and/or networks, different systems, devices, and/or networks, or differently arranged systems, devices, and/or networks than those shown in FIGS. 1 and 2A-2C. Furthermore, two or more systems or devices shown in FIGS. 1 and 2A-C can be implemented within a single system or a single device, or a single system or a single device shown in FIGS. 1 and 2A-2C can be implemented as multiple, distributed systems or devices. Additionally, or alternatively, a set of systems or a set of devices (e.g., one or more systems, one or more devices, etc.) of environment 100 and/or implementation 200 can perform one or more functions described as being performed by another set of systems or another set of devices of environment 100 and/or implementation 200.

Figure 3:
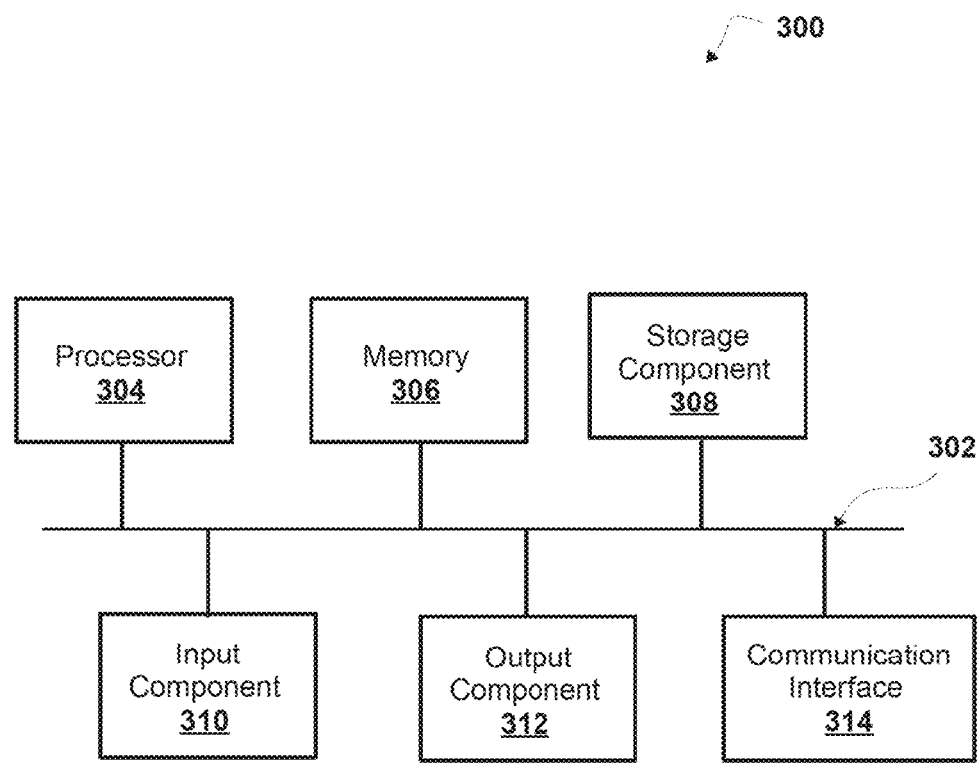
FIG. 3 is a diagram of non-limiting embodiments or aspects of components of one or more devices and/or one or more systems of FIGS. 1 and 2A-2C.

Referring now to FIG. 3, FIG. 3 is a diagram of example components of a device 300. Device 300 may correspond to one or more devices of medication source system 102, smart device 104, and/or one or more devices of communication network 106, one or more devices of central computing system 108, one or more devices of terminal/mobile computing system 110, one or more devices of medication source controller 204, and/or one or more devices of medication source device 206. In some non-limiting embodiments or aspects, one or more devices of medication source system 102, smart device 104, and/or one or more devices of communication network 106, one or more devices of central computing system 108, one or more devices of terminal/mobile computing system 110, one or more devices of medication source controller 204, and/or one or more devices of medication source device 206 can include at least one device 300 and/or at least one component of device 300. As shown in FIG. 3, device 300 may include a bus 302, a processor 304, memory 306, a storage component 308, an input component 310, an output component 312, and a communication interface 314.

Bus 302 may include a component that permits communication among the components of device 300. In some non-limiting embodiments or aspects, processor 304 may be implemented in hardware, firmware, or a combination of hardware and software. For example, processor 304 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), a microcontroller (MCU), etc.) that can be programmed to perform a function. Memory 306 may include random access memory (RAM), read only memory (ROM), and/or another type of dynamic or static storage device (e.g., flash memory, magnetic memory, optical memory, etc.) that stores information and/or instructions for use by processor 304.

Storage component 308 may store information and/or software related to the operation and use of device 300. For example, storage component 308 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 310 may include a component that permits device 300 to receive information, such as via user input (e.g., a touch screen display, a keyboard, a keypad, a mouse, a button, a switch, a microphone, a camera, an electroencephalogram (EEG) monitor, etc.). Additionally, or alternatively, input component 310 may include a sensor for sensing information (e.g., a global positioning system (GPS) component, an accelerometer, a gyroscope, an actuator, etc.). Output component 312 may include a component that provides output information from device 300 (e.g., a display, a speaker, one or more light-emitting diodes (LEDs), and/or the like).

Communication interface 314 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 314 may permit device 300 to receive information from another device and/or provide information to another device. For example, communication interface 314 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 300 may perform one or more processes described herein. Device 300 may perform these processes based on processor 304 executing software instructions stored by a computer-readable medium, such as memory 306 and/or storage component 308. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 306 and/or storage component 308 from another computer-readable medium or from another device via communication interface 314. When executed, software instructions stored in memory 306 and/or storage component 308 may cause processor 304 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 306 and/or storage component 308 may include data storage or one or more data structures (e.g., a database, etc.). Device 300 may be capable of receiving information from, storing information in, communicating information to, or searching information stored in the data storage or one or more data structures in memory 306 and/or storage component 308. For example, the information may input data, output data, medical data, or any combination thereof.

The number and arrangement of components shown in FIG. 3 are provided as an example. In some non-limiting embodiments or aspects, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figures 5A, 5B:
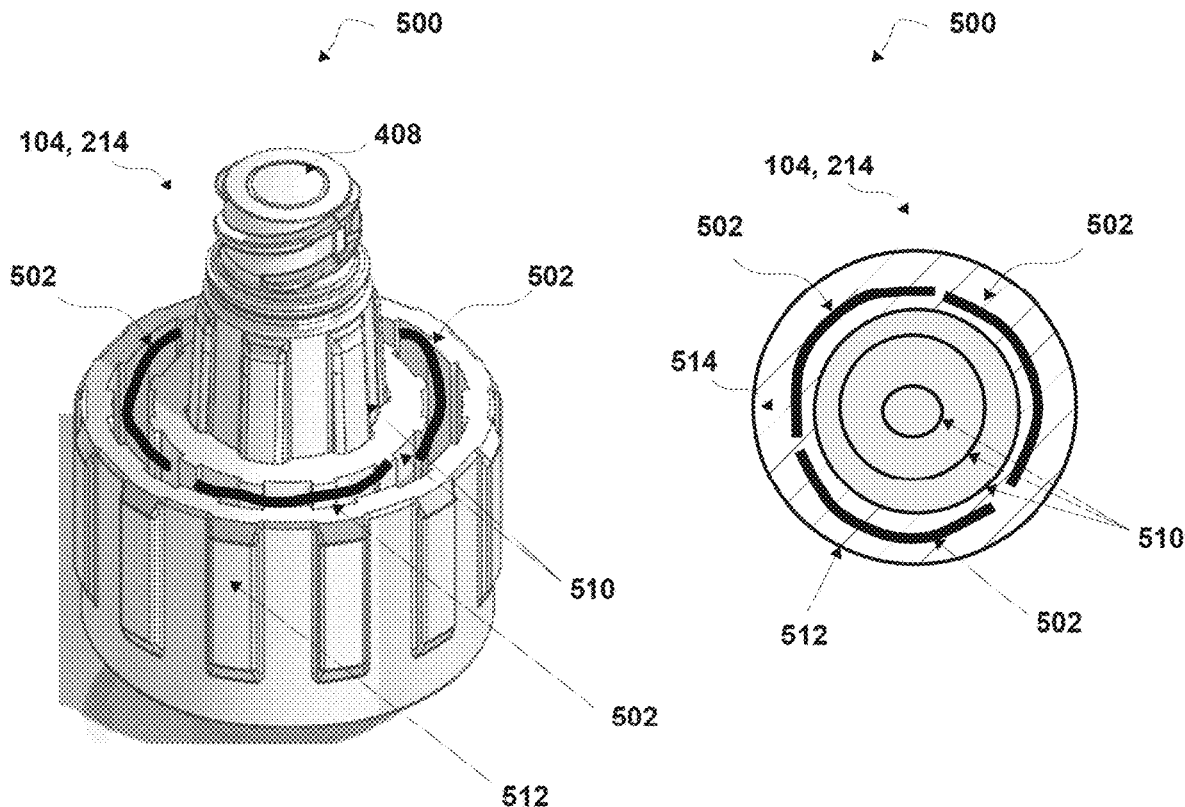
FIG. 5A is a perspective view of non-limiting embodiments or aspects of an implementation of a smart device and a needleless connector.
FIG. 5B is a top view of non-limiting embodiments or aspects of an implementation of a smart device and a needleless connector.
Figure 5C:
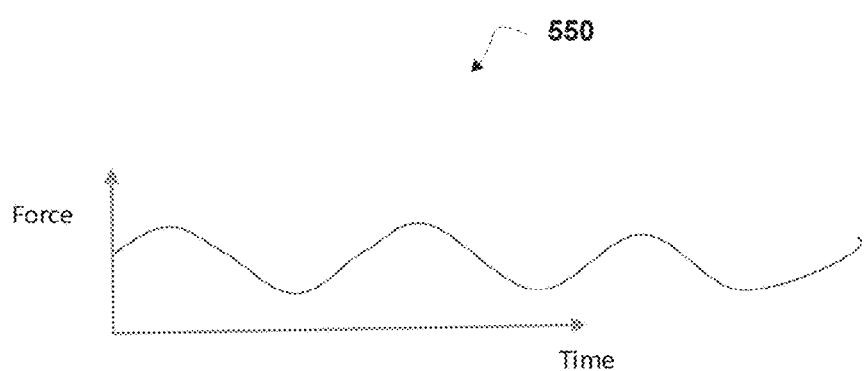
FIG. 5C is a graph of non-limiting embodiments or aspects of a force signal over time.

FIG. 5A is a perspective view and FIG. 5B is a top view of non-limiting embodiments or aspects of an implementation 500 of smart device 104 including needleless connector 214. Referring also to FIG. 4A, needleless connector 214 may include a fluid flow path in housing 402 between inlet 404 and outlet 406 opposite the inlet 404. Inlet 404 may be fluidically sealed by displaceable septum 408 configured to be displaced to open or connect inlet 404 to the fluid flow path in response to connection of needleless connector 214 to a medical device (e.g., an infusion pump, an IV bag, a syringe, an IV line, etc.). Referring again to FIGS. 5A and 5B, in some non-limiting embodiments, smart device 104 may include sensor 254. For example, sensor 254 may include force sensor 502 connected to needleless connector 214. As an example, force sensor 502 may be configured to sense, detect, and/or determine a force signal. In such an example, at least one of: a scrubbing event in which the needleless connector is scrubbed with a disinfectant, a flushing event in which the needleless connector is flushed with a solution, a connection event in which the needleless connector is connected to a medical device, or any combination thereof, may be determined based on the force signal (e.g., by smart device 104, etc.). In such an example, a pattern of events including a plurality of the least one of: the scrubbing event in which the needleless connector is scrubbed with the disinfectant, the flushing event in which the needleless connector is flushed with the solution, the connection event in which the needleless connector is connected to the medical device, a time between one or more detected events, or any combination thereof may be determined based on the force signal, and a medication administration event in which a medication is administered to a patient via needleless connector 214 may be determined based on the pattern of events. As an example, a standard medical practice may assume a Scrub-Flush-Scrub-MedAdmin-Scrub-Flush-Scrub pattern or sequence of events and, therefore, detection of three access of luer connectors may be interpreted by smart device 104 as a medication administration event. For example, FIG. 5C is a graph 550 of non-limiting embodiments or aspects of a force measurement or signal over time. As shown in FIG. FIG. 5C, pulsatile flushing may be determined or detected by force measurement, for example, when flushing is achieved by intermittent pressure pulses applied to a plunger of a flush syringe, and smart device 104 can detect occurrences of pulsatile flushes by identifying periodic force signals between x-y Hz in a force signal perpendicular to a surface of septum 408 of needleless connector 214. For example, smart device 104 may determine, based on the force signal indicating periodic forces in the second direction perpendicular to the surface of the septum facing in the first direction, the flushing event, and that the flushing event includes a pulsatile flushing event.

In some non-limiting embodiment or aspects, smart device may 104 may include communication circuitry configured to transmit the force signal to a remote computing system. For example, medication source system 102, central computing system 108, and/or terminal/mobile computing system 110 may obtain the force signal from smart device 104 and/or needleless connector 214 and process the force signal to determine at least one of: a scrubbing event in which the needleless connector is scrubbed with a disinfectant, a flushing event in which the needleless connector is flushed with a solution, a connection event in which the needleless connector is connected to a medical device, or any combination thereof.

In some non-limiting embodiments or aspects, force sensor 502 includes at least one of: a piezoelectric element, a force sensitive resistive (FSR) sensor, a strain gauge, or any combination thereof. In some non-limiting embodiments or aspects, force sensor 502 is positioned between an outer surface of inner wall 510 (e.g., an inner harder plastic wall) of needleless connector 214 defining the fluid flow path of needleless connector 214 and an inner surface of an outer wall 512 (e.g., a softer, a more flexible, a more pliable, a rubber, etc. wall) of needleless connector 214 surrounding the inner wall 510 of needleless connector 214. In some non-limiting embodiments or aspects, an area between an outer surface of inner wall 510 (e.g., an inner harder plastic wall) of needleless connector 214 defining the fluid flow path of needleless connector 214 and an inner surface of an outer wall 512 (e.g., a softer, a more flexible, more, a more pliable, a rubber, etc. wall) of needleless connector 214 surrounding the inner wall 510 of needleless connector 214, which may be held by a user during cleaning and/or connection to another medical device, may be filled with a rubber or other pliable type material 514 including force sensors 502 as force sensing films within the material 514 between the inner wall 510 and the outer wall 512. In some non-limiting embodiments or aspects, force sensors 502 may be located between inner wall 510 and outer wall 512 below threading on and/or proximal to inlet 404 of needleless connector 214.

In some non-limiting embodiments or aspects, force sensor 502 includes a plurality of force sensors 502 positioned around the fluid flow path of needleless connector 214 between the outer surface of inner wall 510 of needleless connector 214 defining the fluid flow path of needleless connector 214 and the inner surface of outer wall 512 of needleless connector 214 surrounding inner wall 510 of needleless connector 214. For example, inlet 404 of needleless connector 214 may include septum 408 including a surface facing in a first direction, and force sensor 502 may be configured to detect a force in a second direction perpendicular to the surface of the septum facing in the first direction. As an example, the flushing event, which may include a pulsatile flushing event, may be determined based on the force signal indicating periodic forces in the second direction perpendicular to the surface of the septum facing in the first direction.

In some non-limiting embodiments or aspects, sensor 254 includes a pressure sensor, and the pressure sensor is one of: in direct contact with a fluid in the fluid flow path of the needleless connector; located within an inner wall of the needleless connector defining the fluid flow path of the needleless connector, and located within a wall of a lumen connected to the needleless connector. For example, smart device 104 may determine or detect pulsatile flush, a flush, and or a med-administration by the pressure sensor in contact with the fluid path in the needleless connector 214 and/or a lumen thereof.

In some non-limiting embodiments or aspects, sensor 254 includes an optical sensor configured to detect at least one of a color signature and a reflectance of a medical device connected to and/or being connected to needleless connector 214, and smart device 104 may determine a type of the medical device based on the at least one of the color signature and the reflectance of the medical device. For example, a color signature and/or the reflectance of the medical device may be indicative of a syringe, an IV bag, an infusion pump, and/or a particular type thereof.

In some non-limiting embodiments or aspects, sensor 254 includes an identification sensor configured to detect an identification tag on a medical device connected to or being connected to the needleless connector. For example, the identification sensor may include a magnetometer, and the identification tag may include a magnetic material on and/or integrated with needleless connector 214.

In some non-limiting embodiments or aspects, sensor 254 includes a position sensor configured to detect movement of the needleless connector. For example, a movement of the patient, a fall event of the patient, a movement of a bed of the patient may be determined (e.g., by smart device 104, etc.) based on the detected movement of the needleless connector.

In some non-limiting embodiments or aspects, sensor 254 includes an RGB color sensor configured to detect a color of a fluid in the fluid flow path of the needleless connector. For example, at least one of a blood-draw in the needleless connector and a retention of blood in the needleless connector may be determined (e.g., by smart device 104, etc.) based on the color of the fluid detected in the fluid flow path of the needleless connector.

In some non-limiting embodiments or aspects, smart device 104 including needleless connector 214 may include visual indicator 252, and visual indicator 252 may be configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, or any combination thereof. For example, as shown in an implementation 600B in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, and/or a detected connection or capping event (e.g., with processor 304, memory 306, storage component 308, input component 310, output component 312, etc.) to store events and report compliance performance for compliance event monitoring.

Figure 7:
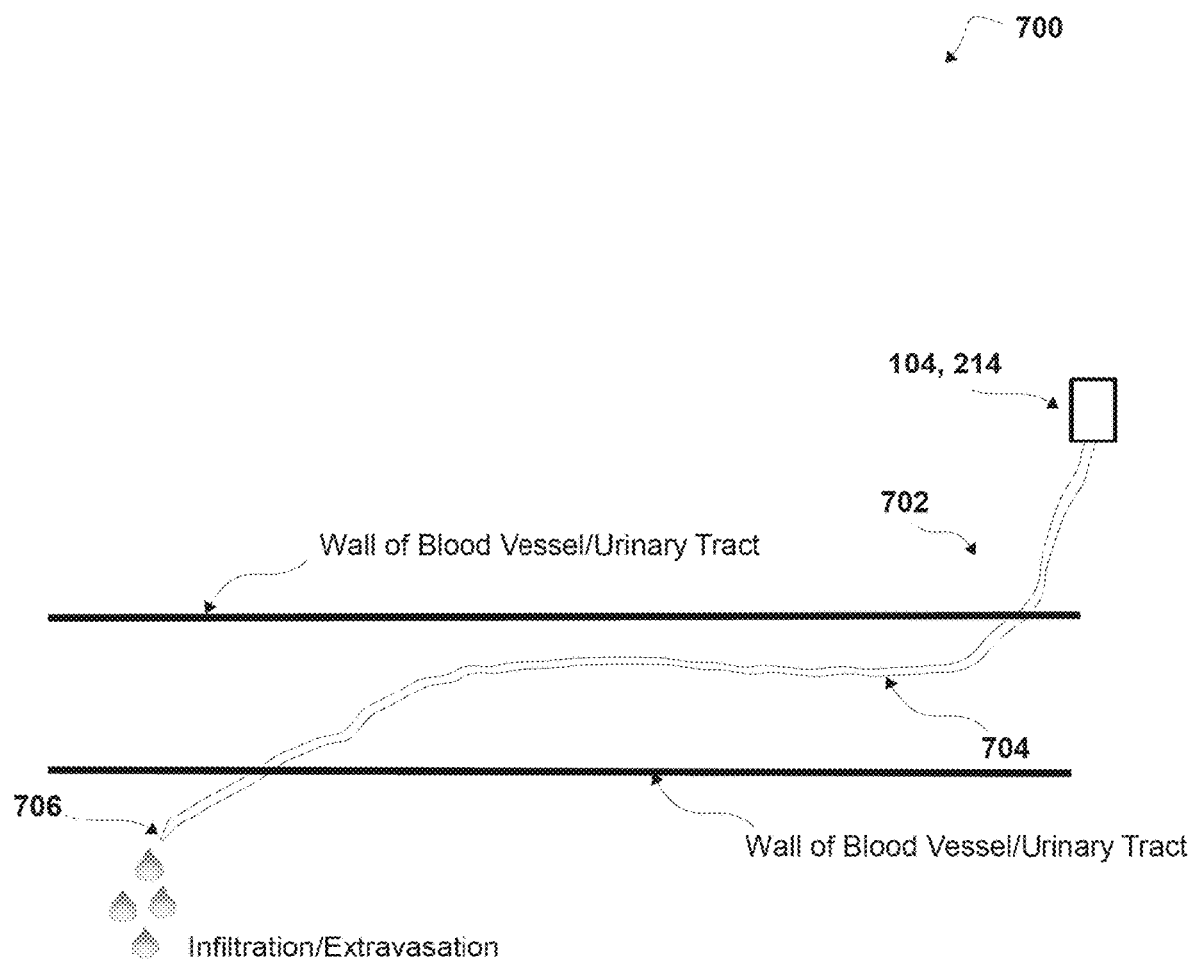
FIG. 7 is a diagram of non-limiting embodiments or aspects of an implementation of a smart device for detecting an extravasation and/or an infiltration of a medication in a catheter.

FIG. 7 is a diagram of non-limiting embodiments or aspects of an implementation 700 of a smart device for detecting an extravasation or an infiltration of a medication in a catheter. As shown in FIG. 7, smart device 104 may be connected to or integrated with a needleless connector 214 at a catheter hub of catheter 702 including a catheter lumen or line 704 and a needle tip 706 for delivering fluid to a patient at an opposite end of the catheter line 704 from smart device 104. Catheter 702 may be inserted in a blood vessel (e.g., a vein, an artery, etc.) or a urinary tract of the patient. For example, the location of the tip 706 of the needle may be within the blood vessel or the urinary tract of the patient, within a wall of the blood vessel or a wall of the urinary tract of the patient, or outside the blood vessel or the urinary tract and the wall of the blood vessel or the wall of the urinary tract of the patient. In some non-limiting embodiments or aspects, smart device 104 including catheter 702 may include a wired and/or a wireless transmitted configured to (e.g., via a wire, wirelessly, etc.) transmit the at least one signal (and/or a variation in the at least one signal over a period of time, a location of the tip of the needle with respect to a blood vessel or a urinary tract of the patient, etc.) to a remote computer system or processing device.

In some non-limiting embodiments or aspects, smart device 104 may include sensor 254 (e.g., as shown in FIG. 3) located outside a body of the patient (e.g., at needleless connector 214 at the hub of catheter 702 located outside of a body of the patient, and sensor 254 may be connected to the hub of catheter 702 outside the body of the patient, etc.). For example, sensor 254 may include at least one of a pressure sensor and an acoustic sensor (e.g., a piezoelectric transducer, etc.). As an example, sensor 254 including the pressure sensor and/or the acoustic sensor may be connected to catheter 802 at needleless connector 214 at the hub of catheter 792. For example, the hub of catheter 702 may include needleless connector 702 and/or smart device 104, and sensor 254 may be included in needleless connector 214. In such an example, sensor 254 may be configured to sense, detect, and/or measure a pressure signal, an acoustic signal, and/or temporal variations in the pressure signal and/or the acoustic signal with the catheter needle in the body of the patient. For example, the pressure signal and/or the acoustic signal sensed by sensor 254 may be transmitted through a fluid in the catheter and/or through material of the catheter (e.g., via needle tip 706, catheter lumen 704, the needleless connector 214, etc.) for sensing by sensor 254. As an example, the pressure signal and/or the acoustic signal sensed by sensor 254 may decrease or drop if needle tip 706 punctures a wall of a blood vessel or urinary tract of the patient. In such an example, a decrease and/or lack in the pressure signal (e.g., a decreased amplitude of a heart rate and/or a drop in blood pressure, etc.) may indicate a lack of a pressure signal associated with an absence of a blood pressure signal, thereby indicating an infiltration event.

In some non-limiting embodiments or aspects, smart device 104 may be programmed and/or configured to compare a relatively slower change or variation in a pressure signal over time (e.g., a relatively slower decrease in an amplitude of a heart rate and/or a drop in blood pressure, etc.) to a threshold level to determine an occlusion event rather than an infiltration event or an extravasation event. For example, an occlusion in a lumen may be at a relatively slow rate over time (e.g., as compared to an infiltration event, an extravasation even, a disconnection event, etc.), which slowly changes the in the pressure signal sensed may sensor 254. As an example, smart device 104 may determine an occlusion even and provide an alter and/or automatically flush a lumen associated with the occlusion in response to detection of the occlusion event. In some non-limiting embodiments, smart device 104 may detect a disconnection event in response to detecting a pressure signal substantially equal to an atmospheric pressure by sensor 254, which indicates that a connection of catheter 702, e.g., needleless connector 214 is disconnected therefrom and provide an alter to a user to address the connection.

In some non-limiting embodiments or aspects, smart device 104 can provide, according the pressure signal and/or the acoustic signal, a location of the tip of the needle with respect to a blood vessel or a urinary tract of the patient in real-time, thereby providing real-time feedback to a user as a catheter is being installed in a blood vessel or a urinary tract of patient to indicate whether the catheter is properly placed within the blood vessel or the urinary tract or if with one of a potential or existing infiltration of the fluid and a potential or existing extravasation of the fluid.

Figure 8:
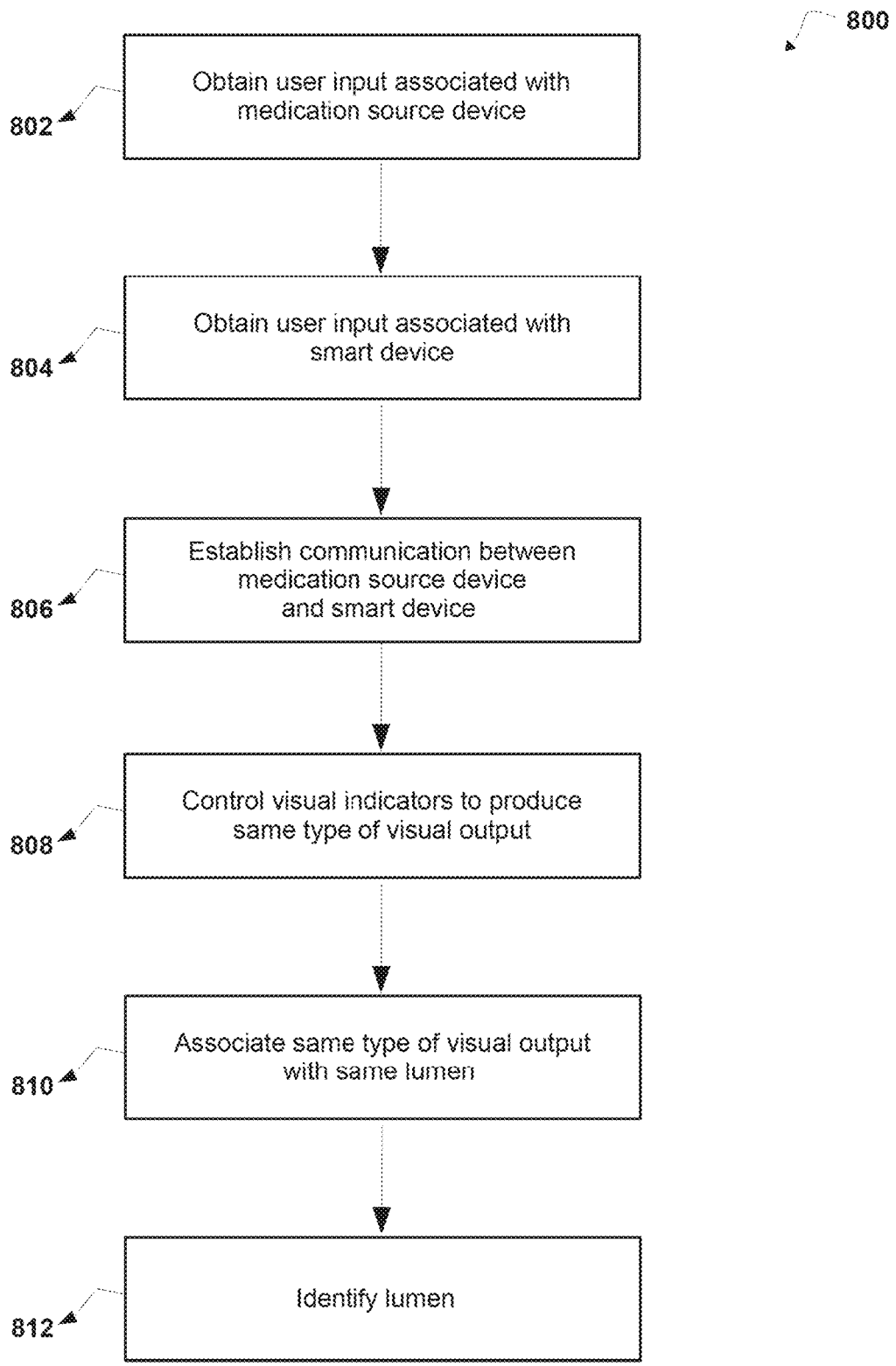
FIG. 8 is a flowchart of non-limiting embodiments or aspects of a process for identifying a lumen.

Referring now to FIG. 8, FIG. 8 is a flowchart of a non-limiting embodiment or aspect of a process 800 for identifying a lumen. In some non-limiting embodiments or aspects, one or more of the steps of process 800 are performed (e.g., completely, partially, etc.) by medication source system 102 (e.g., one or more devices of medication source system 102, etc.). In some non-limiting embodiments or aspects, one or more of the steps of process 800 are performed (e.g., completely, partially, etc.) by another device or a group of devices separate from or including medication source system 102, such as smart device 104 (e.g., one or more devices of a system of smart device 104, etc.), central computing system 108 (e.g., one or more devices of central computing system 108, etc.), and/or terminal/mobile computing system 110 (e.g., one or more devices of terminal/mobile computing system 110, etc.).

As shown in FIG. 8, at step 802, process 800 includes obtaining user input associated with a medication source device. For example, medication source system 102 may obtain user input associated with medication source device 206. As an example, medication source system 102 may obtain (e.g., receive, retrieve, determine, etc.) user input received via a user input component (e.g., via pairing input 208, etc.) of medication source device 206. In such an example, medication source system 102 may receive data associated with the user input from medication source device 206.

Referring also to FIG. 2A, in some non-limiting embodiments or aspects, a plurality of medication source devices 206a, 206b, . . . 206n of a medication source system 102 are connected to a plurality of lumens 212a, 212b, . . . 212n, and each medication source 206 device may include a visual indicator 210, communication circuitry (e.g., communication interface 314, etc.), and a paring input 208. In some non-limiting embodiments or aspects, medication source device 206 receives, via pairing input 208 of medication source device 206, user input. For example, visual indicator 210 may emit a predetermined light pattern (e.g., blink rapidly and/or emit a predetermined color to indicate that medication source device 206 is in a pairing mode, etc.) in response to a predetermined user input to pairing input 208 (e.g., in response to a user pressing and holding a button of pairing input 208, etc.) of medication source device 206.

As shown in FIG. 8, at step 804, process 800 includes obtaining user input associated with a smart device. For example, medication source system 102 may obtain user input associated with smart device 104. As an example, medication source system 102 may obtain (e.g., receive, retrieve, determine, etc.) user input received via a user input component (e.g., pairing input 256, etc.) of smart device 104. In such an example, medication source system 102 may receive data associated with the user input from smart device 104 that is received at a same time that medication source device 206 is in the pairing mode.

Referring also to FIGS. 2A and 2B, in some non-limiting embodiments or aspects, a plurality of smart devices 104a, 104b, . . . 104n may be connected (e.g., removably connected, etc.) or configured to be connected to the plurality of lumens 212a, 212b, . . . 212n, and each smart device 104 may include a visual indicator 252, communication circuitry (e.g., communication interface 314, etc.), and a paring input 256. In some non-limiting embodiments or aspects, smart device 104 receives, via pairing input 256 of smart device 104, user input. For example, smart device 104 may establish communication with medication source device 206 (e.g., pair and/or activate/initiate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

As shown in FIG. 8, at step 806, process 800 includes establishing communication between a medication source device and a smart device. For example, medication source system 102 may establish communication between medication source device 206 and smart device 104. As an example, medication source system 102 may establish communication (e.g., an NFC communication connection, an RFID communication connection, a Bluetooth® communication connection, and/or the like). between medication source device 206 and smart device 104. In such an example, the communication circuitry of smart device 104 and the communication circuitry of medication source device 206 may establish the communication between (e.g., pair, etc.) smart device 104 and medication source device 206 based on the user input received by pairing input 208 of the medication source device 206 and the user input received by pairing input 256 of smart device 104. For example, medication source device 206 may establish a short range wireless communication connection (e.g., an NFC communication connection, an RFID communication connection, a Bluetooth® communication connection, etc.) with smart device 104. As an example, visual indicator 210 may be configured to emit a predetermined light pattern (e.g., to blink rapidly to indicate that medication source device 206 is in a pairing mode, etc.) in response to a predetermined user input to pairing input 208 (e.g., in response to a user pressing and holding a button of pairing input 208, etc.) of medication source device 206. In such an example, smart device 104 may be configured to establish communication with medication source device 206 (e.g., pair and/or activate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

As shown in FIG. 8, at step 808, process 800 includes controlling visual indicators of a medication source device and a smart device to produce a same type of visual output. For example, medication source system 102 may control visual indicator 210 of medication source device 206 and visual indicator 252 of smart device 104 to produce a same type of visual output. As an example, medication source system 102 may control visual indicator 210 (e.g., a multi-color LED, etc.) of medication source device 206 and visual indicator 252 (e.g., a multi-color LED, etc.) of smart device 104 to produce a same type of visual output (e.g., a same color of light, etc.) based on the communication established between the medication source device and the smart device.

In some non-limiting embodiments or aspects, when smart device 104 is paired with medication source device 206, medication source device 206 may illuminate visual indicator 210 to a color that has not been previously used in medication source system 102 (e.g., that is not associated with another medication source device 206 and another smart device 104 that are paired in medication source system 102, that is different than each other color of light produced by each other smart device 104 of the plurality of smart devices 104a, 104b, . . . 104n and each other medication source device 206 of the plurality of medication source devices 206a, 206b, . . . 206n in medication source system 102, etc.), and smart device 104 may illuminate visual indicator 252 to the same color as visual indicator 210 (e.g., medication source system 102, medication source device 206, smart device 104, etc. may control visual indicator 252 5o illuminate to the same color as visual indictor 210). In some non-limiting embodiments or aspects, smart device 104 may illuminate visual indicator 252 to the same color as visual indicator 210 in response to smart device 104 being connected to a lumen and/or during a period of time at which smart device 104 is connected to the lumen. For example, smart device 104 may automatically stop illumination of visual indicator 252 to the same color as visual indicator 210 (e.g., turn off an LED, set the LED to a default color indicating a non-paired smart device 104, etc.) in response to smart device 104 being disconnected from the lumen. As an example, smart device 104 may include a switch connected to visual indicator 252 and configured to be activated/deactivated in response to a clamp or other connection means being connected/disconnected to a lumen and/or a needleless connector 214 thereof.

In some non-limiting embodiments or aspects, medication source system 102 determines a color of the same color of light for visual indicator 252 of smart device 104 and visual indicator 210 of medication source device 206 to produce based on at least one of the user input received by pairing input 208 of medication source device 206 and the user input received by pairing input 256 of smart device 104. For example, after smart device 104 is paired with medication source device 206, a user may actuate pairing input 208 and/or pairing input 256 to cycle through colors of light available for the pairing to select a desired (and/or available or previously unused) color of light for the pairing.

As shown in FIG. 8, at step 810, process 800 includes associating a same type of visual output with a same lumen. For example, medication source system 102 may associate (e.g., automatically associate, etc.) a same type of visual output with a same lumen. As an example, medication source system 102 may associate (e.g., store in connection with, pair, link, illuminate with, etc.) the same type of visual output (e.g., a same color of light, etc.) with a same lumen (e.g., with a same lumen of a plurality of lumens 212a, 212b, . . . 212n, etc.). In such an example, medication source device 206 and smart device 104 may be connected to the same lumen. Accordingly, a user may more easily identify a lumen or line, a location of the lumen or line, a medication that has been or is being delivered via the lumen or line, which infusion pump or mediation source to which the lumen or line is connected, and/or the like.

In some non-limiting embodiments or aspects, medication source system 102 may obtain user input received by a user input component of another medication source device, obtain user input received by a user input component of another smart device, establish a communication between the another medication source device and the another smart device based on the user input received by the user input component of the another medication source device and the user input received by the user input component of the another smart device, control the visual indicator of the another smart device and the visual indicator of the another medication source device to produce another same type of visual output based on the communication established between the another medication source device and the another smart device, wherein the another same type of visual output is different than the same type of visual output, and/or associate the another same type of visual output with another same lumen of the plurality of lumens, wherein the another medication source device is connected to the another same lumen. For example, and referring again to FIG. 2A, medication source device 206a may be paired with smart device 104n and each of medication source device 206a and smart device 104n may output a first color of light (e.g., red light) associated with lumen 212a, medication source device 206b may be paired with smart device 104a and each of medication source device 206b and smart device 104a may output a second color of light (e.g., green light) associated with lumen 21b, medication source device 206n may be paired with smart device 104b and each of medication source device 206n and smart device 104b may output a third color of light (e.g., blue light) associated with lumen 212n, and/or the like.

As shown in FIG. 8, at step 812, process 800 includes identifying a lumen. For example, medication source system 102 may identify a lumen. As an example, medication source system 102 may identify the same lumen associated with the same type of visual output.

In some non-limiting embodiments or aspects, medication source system 102 identifies a lumen by automatically associating and/or providing medical data with the same type of visual output associated with the lumen and/or an identifier of the lumen. For example, medical data may include at least one of the following: patient data (e.g., an identifier of a particular patient, information and/or data associated with a patient, etc.); medication source data (e.g., an identifier of a particular medication source device 206, etc.); medication data (e.g., an identifier of a type of a medication, a scheduled delivery of a particular medication, a previous delivery of a particular medication, a lumen associated with a medication, etc.); lumen data (e.g., an identifier of a particular lumen, such as the identifier of the same lumen associated with the same type of visual output, etc.); sensor data (e.g., an identifier of a particular sensor 254, information, data, and/or a signal sensed, measured, and/or detected by one or more sensors 254 in one or more smart devices 104, etc.); compliance data (e.g., information or data associated with a scrubbing event in which a needleless connector 214 and/or a lumen is scrubbed with a disinfectant, information or data associated with a flushing event in which a needleless connector 214 and/or a lumen is flushed with a solution, information or data associated with a connection or capping event in which a needleless connector 214 or a lumen is connected to a medical device, etc.); location data (e.g., a location of a patient, a location a previous or scheduled fluid delivery procedure, a location a lumen, a location of a medication source device, etc.); time data (e.g., a time associated with a previous or scheduled fluid delivery procedure, a time of connection of a lumen to medication source device 206, a time of connection of smart device 104 to a lumen, a time of pairing of medication source device 206 and smart device 104, etc.); a location of a tip of a needle of a catheter of a lumen with respect to a blood vessel or urinary tract of the patient; or any combination thereof. As an example, medication source system 102 may obtain medical data from smart device 104, central computing system 108, terminal/mobile computing system 110, one or more databases connected thereto, and/or one or more sensors (e.g., a barcode sensor for scanning a patient identifier, a fluid flow sensor for sensing a flow a fluid, a medication type sensor for sensing a type of a medication, etc.) connected thereto. In such an example, medication source system 102 may identify lumens with information and/or data associated therewith, as well as provide a visual indication of which lumens of a plurality of lumens 212a, 212b, . . . 212n are connected to which medication source devices of a plurality of medication source devices 206a, 206b, 206n, which can enable a user to more easily trace a lumen from a patient to a particular medication source device to which the lumen is connected; connections between lumens and medication source devices to be removed if the patient is moved (e.g., to a new room, to a new floor, to surgery, to the bathroom, etc.) with the same type of visual indicator on a lumen/medication source device pair used to more easily reattach the correct medication source device channel to the correct (e.g., the same as before) lumen; tracking compliance to best practice protocols, for example, by determining if hub scrubbing has occurred and if hub scrubbing occurred effectively (e.g., sufficient pressure, sufficient time scrubbing, etc.) and/or if a device has been flushed, maintained, and/or the like; providing reminders and prescriptive help for protocol adherence, and/or the like.

In some non-limiting embodiments or aspects, medication source system 102 identifies a lumen by determining and providing, based on the medical data, one or more alerts or reminders associated with the lumen and/or the same type of visual output associated with the lumen, such as a reminder to flush the lumen and/or a needleless connector 214 thereof, a reminder to remove or replace a lumen, med-mined infection prevention guidance, an alert to use a different lumen for delivery of a particular medication to reduce a chance of a chemical occlusion forming, an alert indicating whether to treat a lumen for thrombus occlusion or chemical occlusion, an alert that an occlusion is detected in a lumen, an alert that a location of a tip of a needle connected to the lumen is associated with one of a potential or existing infiltration of the fluid and a potential or existing extravasation of the fluid, and/or the like.

In some non-limiting embodiments or aspects, medication source system 102 identifies a lumen by controlling a medication source device 206 or another medical device (e.g., an electronic valve, etc.), based on the medical data, to inhibit or prevent delivery of a fluid (e.g., a particular medication, a type of medication, etc.) via the lumen.

Further details regarding non-limiting embodiments or aspects of step 812 of process 800 are provided below with regard to FIG. 9.

Figure 9:
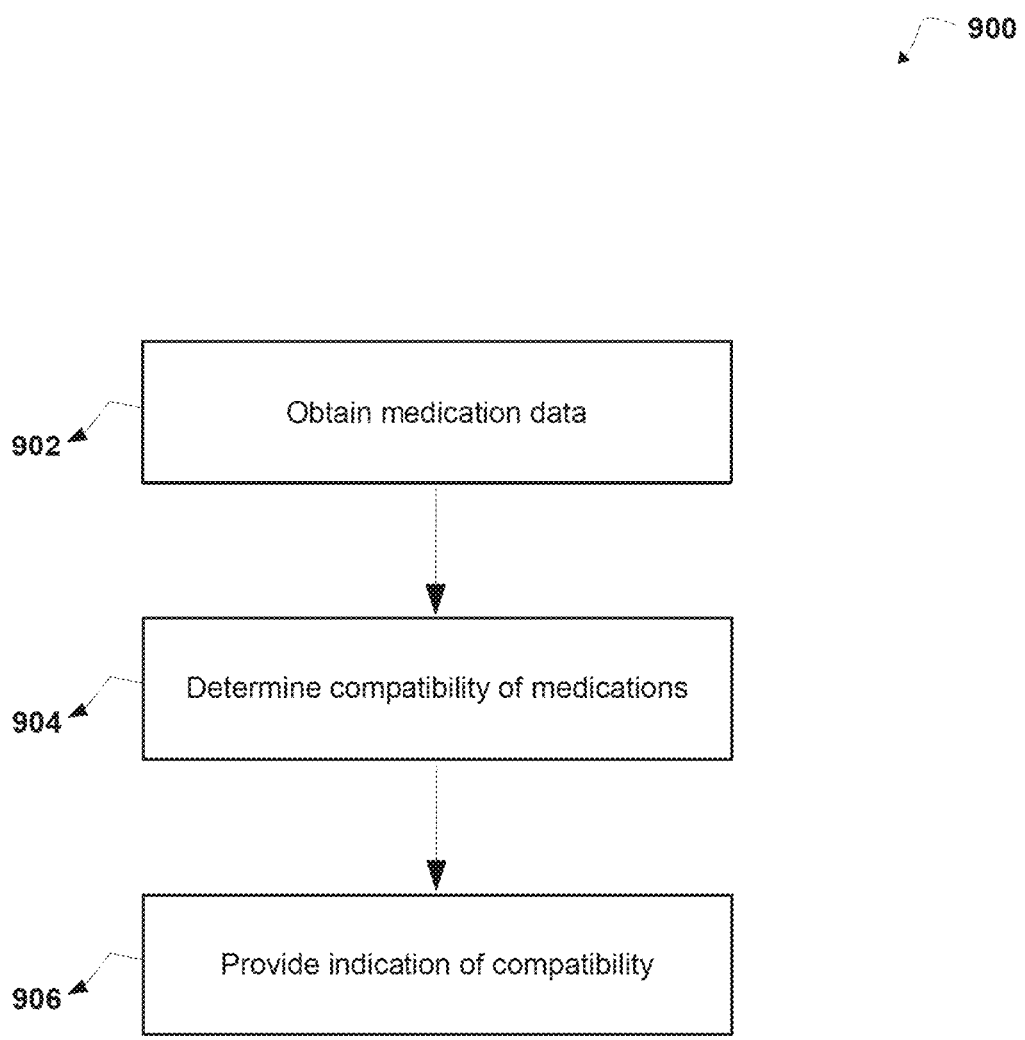
FIG. 9 is a flowchart of non-limiting embodiments or aspects of a process for identifying a lumen.

Referring now to FIG. 9, FIG. 9 is a flowchart of a non-limiting embodiment or aspect of a process 900 for identifying a lumen. In some non-limiting embodiments or aspects, one or more of the steps of process 900 are performed (e.g., completely, partially, etc.) by medication source system 102 (e.g., one or more devices of medication source system 102, etc.). In some non-limiting embodiments or aspects, one or more of the steps of process 900 are performed (e.g., completely, partially, etc.) by another device or a group of devices separate from or including medication source system 102, such as smart device 104 (e.g., one or more devices of a system of smart device 104, etc.), central computing system 108 (e.g., one or more devices of central computing system 108, etc.), and/or terminal/mobile computing system 110 (e.g., one or more devices of terminal/mobile computing system 110, etc.).

As shown in FIG. 9, at step 902, process 900 includes obtaining medication data. For example, medication source system 102 may obtain medication data. As an example, medication source system 102 may obtain medication data associated with a first type of medication delivered or scheduled to be delivered via the same lumen to a patient and a second type of medication delivered or scheduled to be delivered via the same lumen to the patient. In such an example, the first type of medication may be different than the second type of medication.

In some non-limiting embodiments or aspects, medication data is associated with at least one of the following: an identifier of a type of a medication, a scheduled delivery of the medication via a particular medication source device, and/or lumen, a previous delivery of the medication via a particular medication source device and/or lumen, an amount of the medication, an identifier of a patient to which the medication is scheduled to be delivered (or delivered), one or more identifiers of one or more different types of medication that are incompatible for delivery via a same lumen with the medication, and/or the like.

As shown in FIG. 9, at step 904, process 900 includes determining compatibility of medications. For example, medication source system 102 may determine compatibility of medications. As an example, medication source system 102 may determine, based on the medication data, a compatibility of the second type of medication for delivery via the same lumen as the first type of medication.

In some non-limiting embodiments or aspects, medication source system 102 may use an identifier of the first type of medication and/or an identifier of the second type of medication to access a look-up table that indicates whether the first type of medication and the second type of medication are compatible or incompatible (e.g., compatible or incompatible for delivery via a same lumen, etc.). In some non-limiting embodiments or aspects, the look-up table maybe be stored in and/or associated with the identifier of the first type of medication and/or the identifier of the second type of medication.

In some non-limiting embodiments or aspects, medication source device 102 may obtain medication data associated with a third type of medication delivered or scheduled to be delivered via another same lumen (e.g., different than the same lumen, etc.) to the patient, and determine, based on the medication data, a compatibility of the second type of medication for delivery via the another same lumen as the third type of medication, wherein the indication further indicates whether the second type of medication is compatible for delivery via the another same lumen associated with the another same type of visual output. For example, and referring again to FIGS. 2A and 2B, if medication source device 102 determines that the second type of medication is incompatible for delivery via a first lumen 212a, medication source device 102 may determine a compatibility of the second type of medication for delivery via an alternative lumen, such as a second lumen 212b based a third type of medication delivered or scheduled to be delivered via the second lumen 212b and, if the second type of medication is compatible for delivery via the same lumen as the third type of medication, provide the indication that the second type of medication is compatible for delivery via the second lumen 212b.

As shown in FIG. 9, at step 906, process 900 includes providing an indication of compatibility. For example, medication source system 102 may provide an indication of compatibility. As an example, medication source system 102 may provide an indication of whether the second type of medication is compatible for delivery via the same lumen associated with the same type of visual output. As another example, medication source system 102 may provide an indication of whether the third type of medication is compatible for delivery via the another same lumen associated with the another same time of visual output.

In some non-limiting embodiment or aspects, medication source system 102 may provide the indication of the compatibility by controlling medication source device 206 to inhibit or prevent delivery of the second medication via the same lumen associated with the same type of visual output. For example, the first type of medication may be delivered to the patient with the same lumen associated with the same type of visual output, and the second type of medication may be scheduled to be delivered via the same lumen to the patient. As an example, and referring again to FIGS. 2A and 2B, medication source system 102 may determine, based on the medical data including the medication data, that a first type of drug is delivered via lumen 212a to the patient and that a second type of drug that is scheduled for delivery or attempting to be delivered via the same lumen 212a is incompatible with the first type of drug (e.g., likely to cause an occlusion, likely to cause an adverse reaction in the patient, etc.). In such an example, medication source system 102 may control medication source device 206a to inhibit or prevent delivery of the second medication via the same lumen 212a (e.g., by stopping a pump, closing a valve, etc.) and/or providing a prompt to the user to use another lumen (e.g., 212b, . . . 212n, etc.) associated with a different type of visual output than the same type of visual output to deliver the second type of medication to the patient.

In some non-limiting embodiments or aspects, the first type of medication and the second type of medication may be delivered to the patient via the same lumen associated with the same type of visual output, and medication source system 102 may provide a prompt to the user to treat the same lumen associated with the same type of visual output for one of a thrombus occlusion and a chemical occlusion. For example, when an occlusion occurs, which may be detected by medication source system 102 as described herein, a user (e.g., a nurse, etc.) may need to determine if the occlusion is thrombotic or chemical due to drug interactions, and medication source system 102 can determine which medications were delivered via which lumens to inform the user of the lumen history and/or provide an indication of a potential cause of the occlusion, which enables a correct decision of whether the lumen should be treated for thrombus or chemical occlusion. In some non-limiting embodiments or aspects, medication source system 102 may control medication source device 206 to automatically perform a flushing operation to deliver a flushing fluid to a lumen connected to the medication source device 206 in response to a determination that an occlusion of the lumen is a chemical occlusion.

Figure 10:
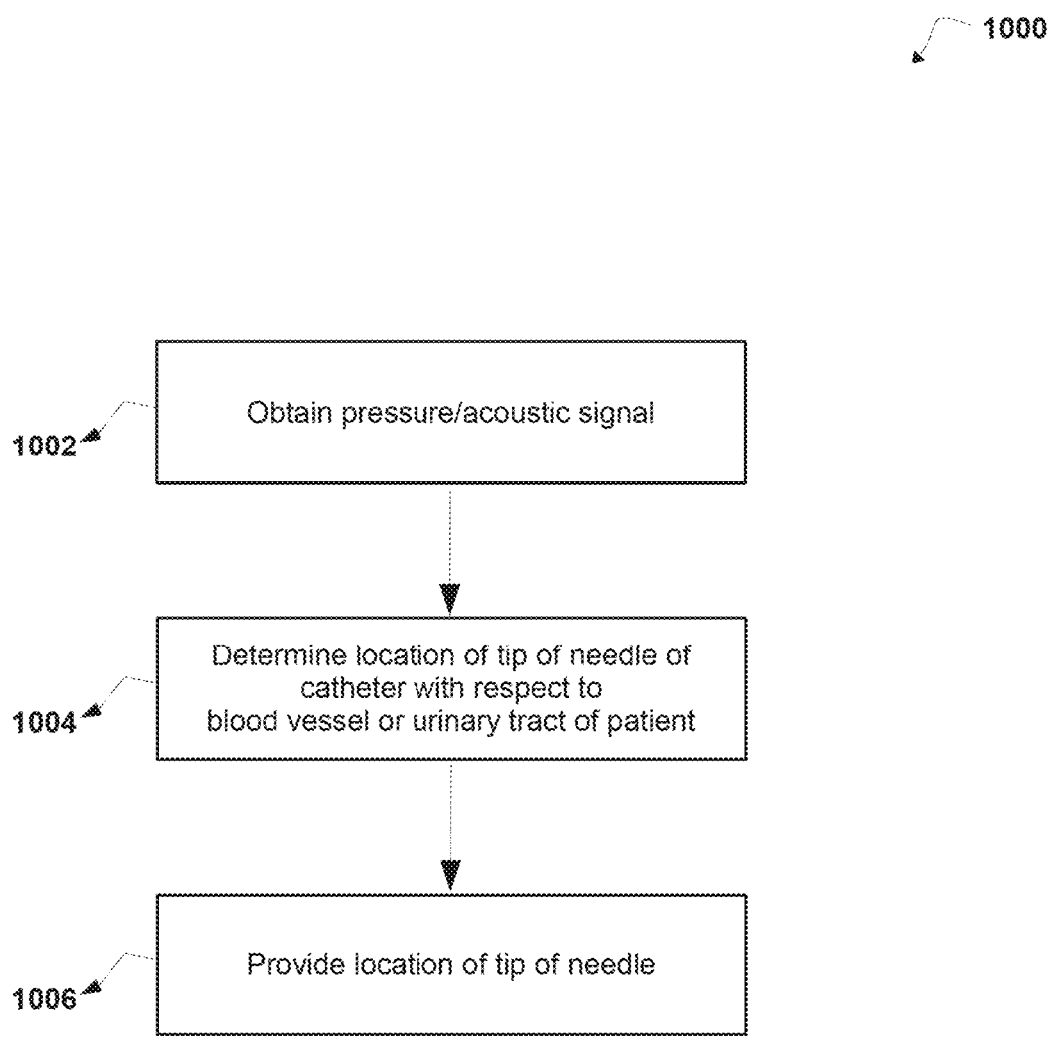
FIG. 10 is a flowchart of non-limiting embodiments or aspects of a process for locating a needle tip.

Referring now to FIG. 10, FIG. 10 is a flowchart of a non-limiting embodiment or aspect of a process 1000 for locating a needle tip. In some non-limiting embodiments or aspects, one or more of the steps of process 1000 are performed (e.g., completely, partially, etc.) by smart device 104 (e.g., one or more devices of a system of smart device 104, etc.). In some non-limiting embodiments or aspects, one or more of the steps of process 1000 are performed (e.g., completely, partially, etc.) by another device or a group of devices separate from or including smart device 104, such as medication source system 102 (e.g., one or more devices of medication source system 102, etc.), central computing system 108 (e.g., one or more devices of central computing system 108, etc.), and/or terminal/mobile computing system 110 (e.g., one or more devices of terminal/mobile computing system 110, etc.).

As shown in FIG. 10, at step 1002, process 1000 includes obtaining a signal including at least one of a pressure signal and an acoustic signal. For example, smart device 104 may obtain a signal including at least one of a pressure signal and an acoustic signal from at least one sensor connected to a catheter. As an example, smart device 104 may obtain at least one signal including at least one of a pressure signal and an acoustic signal from sensor 254 (e.g., from a pressure sensor, from an acoustic sensor, etc.) connected to catheter 702. In some non-limiting embodiments or aspects, and referring also to FIG. 7, catheter 702 includes a needle having tip 706 for delivering a fluid to a patient.

In some non-limiting embodiments or aspects, sensor 254 measures at least one signal including at least one of a pressure signal and an acoustic signal. For example, sensor 254 may measure the at least one signal including at least one of a pressure signal and an acoustic signal, and smart device 104 (and/or medication source system 102, central computing system 108, and/or terminal/mobile computing system 110) may obtain the at least one signal including at least one of a pressure signal and an acoustic signal from sensor 254. For example, smart device 104 may include communication circuitry (e.g., communication interface 314, etc.) that wirelessly transmits the at least one signal to a remote computing system. As an example, smart device 104 may process the pressure signal and/or the acoustic signal on a microprocessor within a housing of smart device 104 including sensor 254 and the microprocessor, and/or smart device 104 may wirelessly transmit (and/or transmit via wired connection) the pressure signal and/or the acoustic signal to a remote computer that perform digital signal processing on the pressure signal and/or the acoustic signal, to identify and classify events of interest (e.g., infiltration, extravasation, catheter occlusion, etc.).

As shown in FIG. 10, at step 1004, process 1000 includes determining a location of a tip of a needle of a catheter with respect to a blood vessel or a urinary tract of a patient. For example, smart device 104 may determine a location of a tip of a needle with respect to a blood vessel or a urinary tract of a patient. As an example, smart device 104 may determine, based on a variation in the at least one signal over a period of time, a location of tip 706 of the needle with respect to a blood vessel or a urinary tract of the patient.

In some non-limiting embodiments or aspects, the location of tip 706 of the needle is determined as one of: within the blood vessel or the urinary tract; within a wall of the blood vessel or a wall of the urinary tract; and outside the blood vessel or the urinary tract and the wall of the blood vessel or the wall of the urinary tract. In some non-limiting embodiments or aspects, smart device 104 and/or one or more components thereof may be connected to or included in (e.g., be integrated with, etc.) a needleless connector 214 at a catheter hub of catheter 702 located outside the body of the patient. For example, sensor 254 of smart device 104 (e.g., a pressure sensor, an acoustic sensor, etc.) may measure at least one signal including at least one of a pressure signal and an acoustic signal, wherein the catheter includes a needle having a tip for delivering a fluid to a patient.

In some non-limiting embodiments or aspects, smart device 104 determines that the location of tip 706 of the needle is associated with one of a potential or existing infiltration of the fluid and a potential or existing extravasation of the fluid. For example, sensor 254 (e.g., one or more pressure sensors, one or more acoustic sensors, etc.) may detect temporal variations in a pressure signal and/or an acoustic signal resulting from tip 706 of the needle of the catheter 702 being properly inserted in a blood vessel or urinary tract, being located in a wall of the blood vessel or urinary tract, being located outside the blood vessel or urinary tract, and/or the like. As an example, smart device 104 may compare the variation in the at least one signal over the period of time to a threshold variation associated with a heartbeat of the patient. For example, the variations in a pressure signal and/or an acoustic signal may be associated with variations in pressure and/or acoustics in a blood vessel or urinary tract as a result of a heartbeat of the patient. As an example, smart device 104 may compare the variations in the detected pressure signal and/or the detected acoustic signal to variations in a pressure signal and/or an acoustic associated with a heartbeat of the patient to determine if tip 706 of the needle of catheter 702 is properly located within the blood vessel (e.g., artery, vein, etc.) of the patient. In such an example, if tip 706 of the needle of catheter 702 overshoots the vessel or urinary tract (e.g., punctures a wall of the blood vessel or urinary tract, is not properly within the blood vessel or urinary tract, etc.) the pressure and/or acoustic signature of the at least one signal measured by sensor 254 changes. In some non-limiting embodiments or aspects, infiltration or extravasation of medication into tissues surrounding the blood vessel or urinary tract (rather than into the blood vessel or urinary tract) may result in distinctive pressure or acoustic signals being detected by sensor 254 depending upon the impact of the infiltration or extravasation on surrounding tissues (e.g., if the extravasating medication is a strong vesicant agent such impacts may be severe, etc.).

In some non-limiting embodiments or aspects, smart device 104 determines, based on the variation in the at least one signal over the period of time, at least one of an occlusion of the catheter and a disconnection of the catheter from a needleless connector. For example, smart device 104 may compare the variation in the at least one signal over the period of time to a threshold period of time associated with formation of an occlusion in a catheter. As an example, smart device 104 may compare a relatively slower change or variation in a pressure signal over time (e.g., a relatively slower decrease in an amplitude of a heart rate and/or a drop in blood pressure as compared to an infiltration or extravasation, etc.) to a threshold level to determine an occlusion event rather than an infiltration event or an extravasation event. For example, an occlusion in a lumen may develop at a relatively slow rate over time (e.g., as compared to an infiltration event, an extravasation even, a disconnection event, etc.), which slowly changes the pressure signal sensed may sensor 254. As an example, smart device 104 may determine an occlusion event and provide an alert and/or automatically flush a lumen associated with the occlusion in response to detection of the occlusion event. In some non-limiting embodiments, smart device 104 may detect a disconnection event in response to detecting a pressure signal substantially equal to an atmospheric pressure by sensor 254, which indicates that a connection of catheter 702, e.g., needleless connector 214 is disconnected therefrom and provide an alter to a user to address the connection.

As shown in FIG. 10, at step 1006, process 1000 includes providing a location of a tip of a needle. For example, smart device 104 may provide a location of a tip of a needle. As an example, smart device 104 may provide the location of tip 706 of the needle with respect to the blood vessel or urinary tract of the patient.

In some non-limiting embodiments or aspects, smart device 104 controls a warning device to issue a warning associated with the one of the potential or existing infiltration of the fluid and the potential or existing extravasation of the fluid. For example, smart device 104 controls visual indicator 252 of smart device 104 to output a color and/or a pattern of light associated with the one of the potential or existing infiltration of the fluid and the potential or existing extravasation of the fluid. As an example, in response to determining an event as infiltration, extravasation, or catheter occlusion, smart device 104 may flash a warning light to a user (e.g., a clinician, a caregiver, a family member, another patient in a homecare or assisted living environment, etc.) and/or transmit a signal to a remote computing system (e.g., medication source system 102, central computing system 108, terminal/mobile computing system 110, etc.) to control (e.g., trigger) output of an audio and/or visual alarm at the remote computing system to alert appropriate individuals of the determined event.

In some non-limiting embodiments or aspects, smart device 104 controls medication source device 206 or a valve (e.g., a valve controlling fluid delivery to/from catheter 702, etc.) to stop (e.g., inhibit, prevent, etc.) delivery of the fluid to the catheter and/or from the catheter. As an example, in response to determining an event as infiltration, extravasation, catheter occlusion, or catheter disconnection smart device 104 may send a signal to an infusion device to immediately stop medication infusion or send a signal to a valve or mechanical clamp to block further medication from infusing into the catheter and/or the patient.

In some non-limiting embodiments or aspects, smart device 104 and/or needleless catheter may include communication circuitry (e.g., communication interface 314, etc.) that wirelessly transmits the at least one signal to a remote computing system. As an example, smart device 104 and/or needleless connector 214 may process the pressure signal and/or the acoustic signal on a microprocessor within housing 250 of smart device 104 and/or within housing 402 of needleless connector 214 including sensor 254 and the microprocessor, and/or smart device 104 and/or needleless connector 214 may wirelessly transmit (and/or transmit via a wired connection) the pressure signal and/or the acoustic signal to a remote computer that performs digital signal processing on the pressure signal and/or the acoustic signal, to identify and classify events of interest (e.g., infiltration, extravasation, catheter occlusion, catheter disconnection, etc.).

In some non-limiting embodiments or aspects, smart device 104 may provide real-time feedback during catheter insertion (e.g., via visual indicator 252, output component 312, medication source system 102, etc.) such that a clinician or other person may be alerted as to whether catheter 702 is being properly inserted and/or as to whether tip 706 of the needle of catheter 702 has pierced or is in the process of piercing a blood vessel or a urinary tract and/or has been accidentally disconnected or occluded.

Figure 11:
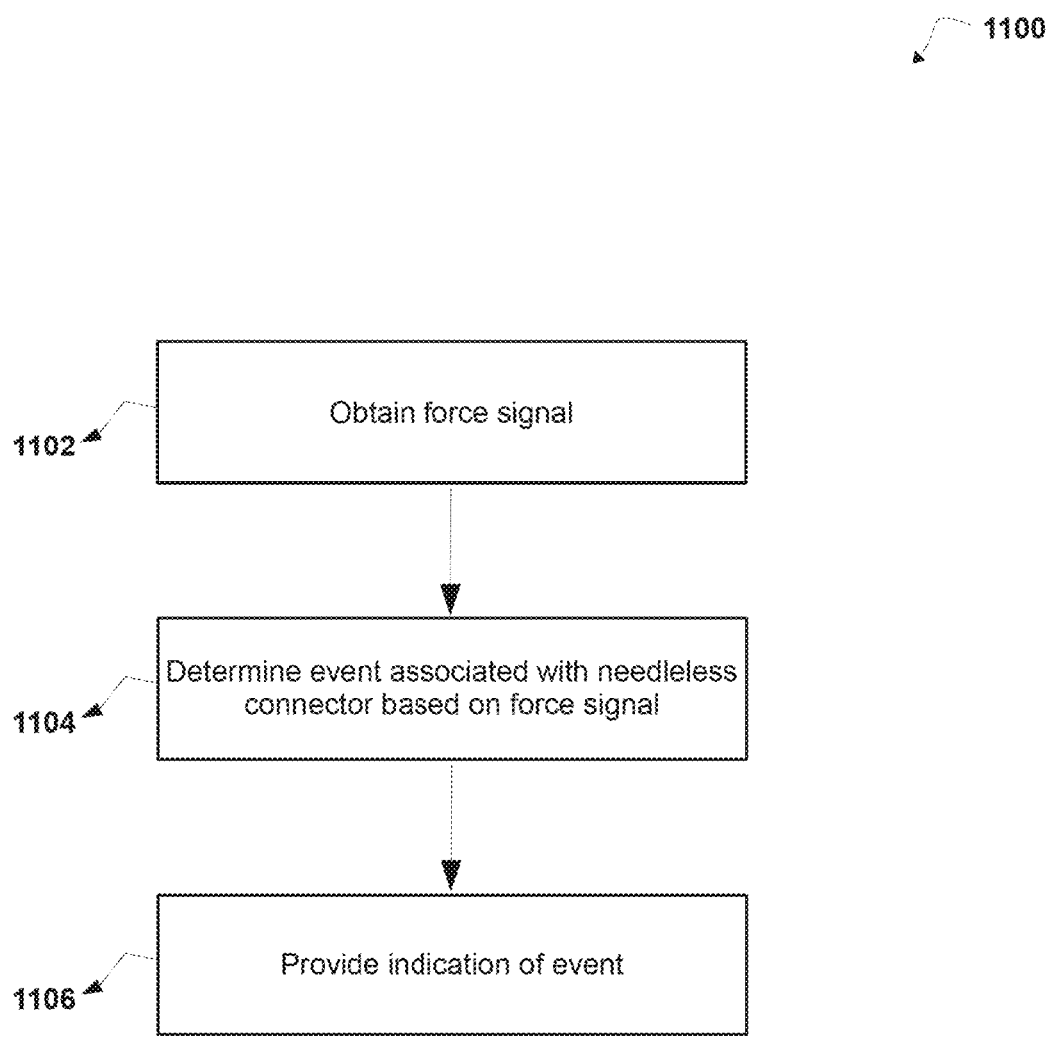
FIG. 11 is a flowchart of non-limiting embodiments or aspects of a process for event monitoring.

Referring now to FIG. 11, FIG. 11 is a flowchart of a non-limiting embodiment or aspect of a process 1100 for compliance event monitoring. In some non-limiting embodiments or aspects, one or more of the steps of process 1100 are performed (e.g., completely, partially, etc.) by smart device 104 (e.g., one or more devices of a system of smart device 104, etc.). In some non-limiting embodiments or aspects, one or more of the steps of process 1100 are performed (e.g., completely, partially, etc.) by another device or a group of devices separate from or including smart device, such as medication source system 102 (e.g., one or more devices of medication source system 102, etc.), central computing system 108 (e.g., one or more devices of central computing system 108, etc.), and/or terminal/mobile computing system 110 (e.g., one or more devices of terminal/mobile computing system 110, etc.).

As shown in FIG. 11, at step 1102, process 1100 includes obtaining a force signal. For example, smart device 104 may obtain a force signal. As an example, smart device 104 may obtain a force signal measured by a sensor 252 (e.g., a force sensor, etc.) connected to a needleless connector 214 including a fluid flow path. In such an example, sensor 252 may measure, with a force sensor connected to a needleless connector including a fluid flow path, a force signal, and smart device 104 (and/or medication source system 101, central computing system 108, terminal/mobile computing system 100, etc.) may obtain the force signal from sensor 252.

As shown in FIG. 11, at step 1104, process 1100 includes determining an event associated with a needleless connector based on a force signal. For example, smart device 104 may determine an event associated with a needleless connector 214 based on a force signal. As an example, smart device 104 may determine, based on the force signal, at least one of: a scrubbing event in which the needleless connector is scrubbed with a disinfectant, a flushing event in which the needleless connector is flushed with a solution, a connection event in which the needleless connector is connected to a medical device, or any combination thereof.

In some non-limiting embodiments or aspects, force sensor 502 includes at least one of: a piezoelectric element, a force sensitive resistive (FSR) sensor, a strain gauge, or any combination thereof. In some non-limiting embodiments or aspects, force sensor 502 is positioned between an outer surface of inner wall 510 (e.g., an inner harder plastic wall) of needleless connector 214 defining the fluid flow path of needleless connector 214 and an inner surface of an outer wall 512 (e.g., a softer, a more flexible, a more pliable, a rubber, etc. wall) of needleless connector 214 surrounding the inner wall 510 of needleless connector 214. In some non-limiting embodiments or aspects, an area between an outer surface of inner wall 510 (e.g., an inner harder plastic wall) of needleless connector 214 defining the fluid flow path of needleless connector 214 and an inner surface of an outer wall 512 (e.g., a softer, a more flexible, more, a more pliable, a rubber, etc. wall) of needleless connector 214 surrounding the inner wall 510 of needleless connector 214, which may be held by a user during cleaning and/or connection to another medical device, may be filled with a rubber or other pliable type material 514 including force sensors 502 as force sensing films within the material 514 between the inner wall 510 and the outer wall 512. In some non-limiting embodiments or aspects, force sensors 502 may be located between inner wall 510 and outer wall 512 below threading on and/or proximal to inlet 404 of needleless connector 214.

In some non-limiting embodiments or aspects, force sensor 502 includes a plurality of force sensors 502 positioned around the fluid flow path of needleless connector 214 between the outer surface of inner wall 510 of needleless connector 214 defining the fluid flow path of needleless connector 214 and the inner surface of outer wall 512 of needleless connector 214 surrounding inner wall 510 of needleless connector 214. For example, inlet 404 of needleless connector 214 may include septum 408 including a surface facing in a first direction, and force sensor 502 may be configured to detect a force in a second direction perpendicular to the surface of the septum facing in the first direction. As an example, the flushing event, which may include a pulsatile flushing event, may be determined based on the force signal indicating periodic forces in the second direction perpendicular to the surface of the septum facing in the first direction.

In some non-limiting embodiments or aspects, sensor 254 includes a pressure sensor, and the pressure sensor is one of: in direct contact with a fluid in the fluid flow path of the needleless connector; located within an inner wall of the needleless connector defining the fluid flow path of the needleless connector, and located within a wall of a lumen connected to the needleless connector. For example, smart device 104 may determine or detect pulsatile flush, a flush, and or a med-administration by the pressure sensor in contact with the fluid path in the needleless connector 214 and/or a lumen thereof.

In some non-limiting embodiments or aspects, sensor 254 includes an optical sensor configured to detect at least one of a color signature and a reflectance of a medical device connected to and/or being connected to needleless connector 214, and smart device 104 may determine a type of the medical device based on the at least one of the color signature and the reflectance of the medical device. For example, a color signature and/or the reflectance of the medical device may be indicative of a syringe, an IV bag, an infusion pump, and/or a particular type thereof.

In some non-limiting embodiments or aspects, sensor 254 includes an identification sensor configured to detect an identification tag on a medical device connected to or being connected to the needleless connector. For example, the identification sensor may include a magnetometer, and the identification tag may include a magnetic material on and/or integrated with needleless connector 214.

In some non-limiting embodiments or aspects, sensor 254 includes a position sensor configured to detect movement of the needleless connector. For example, a movement of the patient, a fall event of the patient, a movement of a bed of the patient may be determined (e.g., by smart device 104, etc.) based on the detected movement of the needleless connector.

In some non-limiting embodiments or aspects, sensor 254 includes an RGB color sensor configured to detect a color of a fluid in the fluid flow path of the needleless connector. For example, at least one of a blood-draw in the needleless connector and a retention of blood in the needleless connector may be determined (e.g., by smart device 104, etc.) based on the color of the fluid detected in the fluid flow path of the needleless connector.

As shown in FIG. 11, at step 1106, process 1100 includes providing an indication of an event. For example, smart device 104 may provide an indication of an event. As an example, smart device 104 may provide an indication of the determined event.

In some non-limiting embodiments or aspects, smart device 104 including needleless connector 214 may include visual indicator 252, and visual indicator 252 may be configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, or any combination thereof. For example, as shown in an implementation 600B in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, and/or a detected connection or capping event (e.g., with processor 304, memory 306, storage component 308, input component 310, output component 312, etc.) to store events and report compliance performance for compliance event monitoring.

In some non-limiting embodiments or aspects, smart device 104 may include communication circuitry (e.g., communication interface 314, etc.) that wirelessly transmits the force signal and/or an event determined based thereon to a remote computing system. As an example, smart device 104 may process the force on a microprocessor within a housing of smart device 104 including sensor 254 and the microprocessor, and/or smart device 104 may wirelessly transmit (and/or transmit via wired connection) the force signal to a remote computer that perform digital signal processing on the force, to identify and classify events of interest (e.g., a scrubbing even, a flushing event, a connection event, etc.).

In some non-limiting embodiments or aspects, a pattern of events including a plurality of the least one of: the scrubbing event in which needleless connector 214 is scrubbed with the disinfectant, the flushing event in which needleless connector 214 is flushed with the solution, connection or capping event in which needleless connector 214 is connected to the medical device, or any combination thereof, may be determined based on the force signal, and, based on the pattern of events, a medication administration event in which a medication is administered to a patient via needleless connector 214 may be determined.

In some non-limiting embodiments or aspects, smart device 104 may use sensor 254 to detect an identification tag on a medical device connected to or being connected to the needleless connector, movement of the needleless connector, a color of a fluid in the fluid flow path of the needleless connector, or any combination thereof, and provide, with visual indicator 252 visual indication associated with the any information or data sensed and/or measured by sensor 254, such as, a type of the medical device, a medication administration event in which a medication is administered to a patient via the needleless connector, an identification of a medical device, a movement of the patient, a patient fall event, a movement of a bed of the patient, a color of a fluid in the fluid flow path of needleless connector 412, a blood-draw in the needleless connector, a retention of blood in the needleless connector, a scrubbing event in which the needleless connector is scrubbed with a disinfectant, a flushing event in which the needleless connector is flushed with a solution, a connection or capping event in which the needleless connector is connected to a medical device, or any combination thereof.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system comprising:
    a plurality of smart devices configured to be connected to a plurality of lumens, wherein each smart device includes a visual indicator, communication circuitry, and a user input component configured to receive a user input from a user;
    a medication source system including a plurality of medication source devices connected to the plurality of lumens, wherein each medication source device includes a visual indicator, communication circuitry, and a user input component configured to receive a user input from the user, wherein the communication circuitry of a medication source device is configured to establish communication with the communication circuitry of a smart device based on the user input to the user input component of the medication source device and the user input to the user input component of the smart device; and
    one or more processors programmed and/or configured to:
        control the visual indicator of the smart device and the visual indicator of the medication source device to produce a same type of visual output based on a communication established between the communication circuitry of the medication source device and the communication circuitry of the smart device;
        associate the same type of visual output with a same lumen of the plurality of lumens, wherein the medication source device is connected to the same lumen;
        obtain medication data associated with a first type of medication delivered or scheduled to be delivered via the same lumen to a patient and a second type of medication delivered or scheduled to be delivered via the same lumen to the patient, wherein the first type of medication is different than the second type of medication;
        determine, based on the medication data, a compatibility of the second type of medication for delivery via the same lumen as the first type of medication; and
        provide an indication of whether the second type of medication is compatible for delivery via the same lumen associated with the same type of visual output.

2. The system of claim 1, wherein the visual indicator of the smart device includes a light emitting diode, and wherein the same type of visual output is a same color of light.

3. The system of claim 2, wherein the light emitting diode is configured to emit a plurality of different colors of light, and wherein the one or more processors are further programmed and/or configured to:
    determine a color of the same color of light for the visual indicator of the smart device and the visual indicator of the medication source device to produce based on at least one of the user input to the user input component of the medication source device and the user input to the user input component of the smart device.

4. The system of claim 2, wherein the light emitting diode is configured to emit a plurality of different colors of light, and wherein the one or more processors are further programmed and/or configured to:
    determine the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

5. The system of claim 1, wherein the medication source system includes an infusion pump system, and wherein the plurality of medication source devices includes a plurality of infusion pumps.

6. The system of claim 1, wherein the first type of medication is delivered via the same lumen to the patient, wherein the second type of medication is scheduled to be delivered via the same lumen to the patient, and wherein the one or more processors are programmed and/or configured to provide the indication of whether the second type of medication is compatible for delivery via the same lumen associated with the same type of visual output by:
controlling the medication source device to inhibit or prevent delivery of the second medication via the same lumen associated with the same type of visual output.

7. The system of claim 1, wherein the first type of medication is delivered via the same lumen to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

8. The system of claim 1, wherein the first type of medication and the second type of medication is delivered via the same lumen associated with the same type of visual output to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

9. The system of claim 1, wherein the visual indicator of the smart device is configured to produce the same type of visual output as the visual indicator of the medication source device in response to being connected to a lumen at a same time the communication is established between the communication circuitry of the medication source device and the communication circuitry of the smart device, and wherein the visual indicator of the smart device is configured to automatically stop producing the same type of visual output as the visual indicator of the medication source device in response to being disconnected from the lumen.

10. The system of claim 1, wherein the communication circuitry of another medication source device is configured to establish communication with the communication circuitry of another smart device based on the user input to the user input component of the another medication source device and the user input to the user input component of the another smart device, and wherein the one or more processors are further programmed and/or configured to:
control the visual indicator of the another smart device and the visual indicator of the another medication source device to produce another same type of visual output based on the communication established between the communication circuitry of the another medication source device and the communication circuitry of the another smart device, wherein the another same type of visual output is different than the same type of visual output;
associate the another same type of visual output with another same lumen of the plurality of lumens, wherein the another medication source device is connected to the another same lumen;
obtain medication data associated with a third type of medication delivered or scheduled to be delivered via the another same lumen to the patient; and
determine, based on the medication data, a compatibility of the second type of medication for delivery via the another same lumen as the third type of medication, wherein the indication further indicates whether the second type of medication is compatible for delivery via the another same lumen associated with the another same type of visual output.

11. A method, comprising:
connecting a plurality of smart devices to a plurality of lumens, wherein each smart device includes a visual indicator, communication circuitry, and a user input component, connecting a plurality of medication source devices of a medication source system to the plurality of lumens, wherein each medication source device includes a visual indicator, communication circuitry, and a user input component;
receiving, via the user input component of a smart device, user input;
receiving, via the user input component of a medication source device, user input;
establishing, with the communication circuitry of the smart device and the communication circuitry of the medication source device, a communication between the smart device and the medication source device based on the user input received by the user input component of the medication source device and the user input received by the user input component of the smart device;
controlling, with at least one processor, the visual indicator of the smart device and the visual indicator of the medication source device to produce a same type of visual output based on the communication established between the medication source device and the smart device;
associating, with at least one processor, the same type of visual output with a same lumen of the plurality of lumens, wherein the medication source device is connected to the same lumen;
obtaining, with at least one processor, medication data associated with a first type of medication delivered or scheduled to be delivered via the same lumen to a patient and a second type of medication delivered or scheduled to be delivered via the same lumen to the patient, wherein the first type of medication is different than the second type of medication;
determining, with at least one processor, based on the medication data, a compatibility of the second type of medication for delivery via the same lumen as the first type of medication; and
providing, with at least one processor, an indication of whether the second type of medication is compatible for delivery via the same lumen associated with the same type of visual output.

12. The method of claim 11, wherein the visual indicator of the smart device includes a light emitting diode, and wherein the same type of visual output is a same color of light.

13. The method of claim 12, wherein the light emitting diode is configured to emit a plurality of different colors of light, and wherein the method further comprises:

determining, with at least one processor, a color of the same color of light for the visual indicator of the smart device and the visual indicator of the medication source device to produce based on at least one of the user input received by the user input component of the medication source device and the user input received by the user input component of the smart device.

14. The method of claim 12, wherein the light emitting diode is configured to emit a plurality of different colors of light, and wherein the method further comprises:
determining, with at least one processor, the same color of light for the visual indicator of the smart device and the visual indicator of the medication source device to produce as a color of light that is different than each other color of light produced by each visual indicator of each other smart device of the plurality of smart devices and each visual indicator of each other medication source device of the plurality of medication source devices.

15. The method of claim 11, wherein the medication source system includes an infusion pump system, and wherein the plurality of medication source devices includes a plurality of infusion pumps.

16. The method of claim 11, further comprising:
delivering, with the same lumen associated with the same type of visual output, the first type of medication to the patient, wherein the second type of medication is scheduled to be delivered via the same lumen to the patient, and wherein providing the indication of whether the second type of medication is compatible for delivery via the same lumen associated with the same type of visual output further comprises:
controlling the medication source device to inhibit or prevent delivery of the second medication via the same lumen associated with the same type of visual output.

17. The method of claim 11, further comprising:
delivering, with the same lumen associated with the same type of visual output, the first type of medication to the patient, wherein the second type of medication is scheduled to be delivered via the same lumen to the patient, and wherein the indication of whether the second type of medication is compatible for delivery via the same lumen associated with the same type of visual output includes a prompt to the user to use another lumen associated with a different type of visual output than the same type of visual output to deliver the second type of medication to the patient.

18. The method of claim 11, further comprising:
delivering, with the same lumen associated with the same type of visual output, the first type of medication and the second type of medication to the patient, and wherein the indication of whether the second type of medication is compatible for delivery via the same lumen associated with the same type of visual output includes a prompt to the user to treat the same lumen associated with the same type of visual output for one of a thrombus occlusion and a chemical occlusion.

19. The method of claim 11, further comprising:
producing, with the visual indicator of the smart device, the same type of visual output as the visual indicator of the medication source device in response to being connected to a lumen at a same time the communication is established between the medication source device and the smart device; and
automatically stopping, with the visual indicator of the smart device, production of the same type of visual output as the visual indicator of the medication source device in response to being disconnected from the lumen.

20. The method of claim 11, further comprising:
receiving, by the user input component of another smart device, user input;
receiving, by the user input component of another medication source device, user input;
establishing, with the communication circuitry of the another medication source device and the communication circuitry of the another smart device, a communication between the another medication source device and the another smart device based on the user input received by the user input component of the another medication source device and the user input received by the user input component of the another smart device;
controlling, with at least one processor, the visual indicator of the another smart device and the visual indicator of the another medication source device to produce another same type of visual output based on the communication established between the another medication source device and the another smart device, wherein the another same type of visual output is different than the same type of visual output;
associating, with at least one processor, the another same type of visual output with another same lumen of the plurality of lumens, wherein the another medication source device is connected to the another same lumen;
obtaining, with at least one processor, medication data associated with a third type of medication delivered or scheduled to be delivered via the another same lumen to the patient; and
determining, with at least one processor, based on the medication data, a compatibility of the second type of medication for delivery via the another same lumen as the third type of medication, wherein the indication further indicates whether the second type of medication is compatible for delivery via the another same lumen associated with the another same type of visual output.

21. A system, comprising:
one or more processors programmed and/or configured to:
control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen;
associate the same type of visual output with the lumen;
obtain medication data associated with a first type of medication delivered or scheduled to be delivered via the lumen to a patient and a second type of medication delivered or scheduled to be delivered via the lumen to the patient, wherein the first type of medication is different than the second type of medication;
determine, based on the medication data, a compatibility of the second type of medication for delivery via the same lumen as the first type of medication; and
provide an indication of whether the second type of medication is compatible for delivery via the same lumen associated with the same type of visual output.

22. A computer-implemented method, comprising:
controlling, with at least one processor, a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen;

associating, with at least one processor, the same type of visual output with the lumen;

obtaining, with at least one processor, medication data associated with a first type of medication delivered or scheduled to be delivered via the lumen to a patient and a second type of medication delivered or scheduled to be delivered via the lumen to the patient, wherein the first type of medication is different than the second type of medication;

determining, with at least one processor, based on the medication data, a compatibility of the second type of medication for delivery via the same lumen as the first type of medication; and providing, with at least one processor, an indication of whether the second type of medication is compatible for delivery via the same lumen associated with the same type of visual output.

23. A computer program product comprising at least one non-transitory computer-readable medium including program instructions that, when executed by at least one processor, cause the at least one processor to:

control a visual indicator of a smart device and a visual indicator of a medication source device to produce a same type of visual output based on a communication established between communication circuitry of the medication source device and communication circuitry of the smart device, wherein the medication source device is connected to a lumen, and wherein the smart device is configured to be connected to the lumen;

associate the same type of visual output with the lumen;

obtain medication data associated with a first type of medication delivered or scheduled to be delivered via the lumen to a patient and a second type of medication delivered or scheduled to be delivered via the lumen to the patient, wherein the first type of medication is different than the second type of medication;

determine, based on the medication data, a compatibility of the second type of medication for delivery via the same lumen as the first type of medication; and provide an indication of whether the second type of medication is compatible for delivery via the same lumen associated with the same type of visual output.

24. A system, comprising:

one or more processors programmed and/or configured to:

control a visual indicator of a smart device and a visual indicator of a medication source device to produce a same type of visual output based on a communication established between communication circuitry of the medication source device and communication circuitry of the smart device, wherein the medication source device is connected to a lumen, wherein the smart device is configured to be connected to the lumen, wherein each visual indicator includes a light emitting diode, wherein each light emitting diode is configured to emit a plurality of different colors of light, and wherein, in response to the communication established between the communication circuitry of the medication source device and the communication circuitry of the smart device, the at least one processor is configured to determine a same color of light for the visual indicator of the smart device and the visual indicator of the medication source device to produce as a color of light that is different than each other color of light produced by each visual indicator of each other smart device of a plurality of smart devices and each visual indicator of each other medication source device of a plurality of medication source devices by cycling through colors of light available to select a previously unused color of light, wherein the same type of visual output includes the same color of light; and associate the same type of visual output with the lumen; and provide the same type of visual output to a user to identify the lumen to the user.

25. A computer-implemented method, comprising:

controlling, with at least one processor, a visual indicator of a smart device and a visual indicator of a medication source device to produce a same type of visual output based on a communication established between communication circuitry of the medication source device and communication circuitry of the smart device, wherein the medication source device is connected to a lumen, wherein the smart device is configured to be connected to the lumen, wherein each visual indicator includes a light emitting diode, wherein each light emitting diode is configured to emit a plurality of different colors of light, and wherein, in response to the communication established between the communication circuitry of the medication source device and the communication circuitry of the smart device, the at least one processor determines a same color of light for the visual indicator of the smart device and the visual indicator of the medication source device to produce as a color of light that is different than each other color of light produced by each visual indicator of each other smart device of a plurality of smart devices and each visual indicator of each other medication source device of a plurality of medication source devices by cycling through colors of light available to select a previously unused color of light, wherein the same type of visual output includes the same color of light;

associating, with at least one processor, the same type of visual output with the lumen; and providing, with at least one processor, the same type of visual output to a user to identify the lumen to the user.

26. A computer program product comprising at least one non-transitory computer-readable medium including program instructions that, when executed by at least one processor, cause the at least one processor to:

control a visual indicator of a smart device and a visual indicator of a medication source device to produce a same type of visual output based on a communication established between communication circuitry of the medication source device and communication circuitry of the smart device, wherein the medication source device is connected to a lumen, wherein the smart device is configured to be connected to the lumen, wherein each visual indicator includes a light emitting diode, wherein each light emitting diode is configured to emit a plurality of different colors of light, and wherein, in response to the communication established between the communication circuitry of the medication source device and the communication circuitry of the smart device, the program instructions, when executed by the at least one processor, cause the at least one processor to determine a same color of light for the visual indicator of the smart device and the visual indicator of the medication source device to produce as a color of light that is different than each other color of light produced by each visual indicator of each other smart device of a plurality of smart devices and each visual indicator of each other medication source device of a plurality of medication source devices by cycling through colors of light available to select a previously unused color of light, wherein the same type of visual output includes the same color of light;

associate the same type of visual output with the lumen; and provide the same type of visual output to a user to identify the lumen to the user.

* * * * *